(12) United States Patent
Spear et al.

(10) Patent No.: US 10,328,243 B2
(45) Date of Patent: *Jun. 25, 2019

(54) SYSTEM AND METHOD FOR POSITIONING IMPLANTABLE MEDICAL DEVICES WITHIN CORONARY VEINS

(71) Applicant: Medtronic, Inc., Minneapolis, MN (US)

(72) Inventors: Stanten C Spear, Arden Hills, MN (US); James F Kelley, Coon Rapids, MN (US); Kenneth C Gardeski, Plymouth, MN (US); Mohmoud K Seraj, Apex, NC (US); Eric K. Y. Chan, Newark, CA (US)

(73) Assignee: MEDTRONIC, INC., Minneapolis, MN (US)

( * ) Notice: Subject to any disclaimer, the term of this patent is extended or adjusted under 35 U.S.C. 154(b) by 529 days.

This patent is subject to a terminal disclaimer.

(21) Appl. No.: 14/283,303

(22) Filed: May 21, 2014

(65) Prior Publication Data
US 2014/0343549 A1 Nov. 20, 2014

Related U.S. Application Data

(60) Continuation of application No. 12/357,810, filed on Jan. 22, 2009, now Pat. No. 8,734,397, which is a
(Continued)

(51) Int. Cl.
*A61M 25/00* (2006.01)
*A61M 25/06* (2006.01)
(Continued)

(52) U.S. Cl.
CPC ..... *A61M 25/0668* (2013.01); *A61B 18/1492* (2013.01); *A61M 25/008* (2013.01);
(Continued)

(58) Field of Classification Search
CPC .......... A61M 25/0668; A61M 25/0141; A61M 25/008; A61M 25/0138;
(Continued)

(56) References Cited

U.S. PATENT DOCUMENTS 4,215,703 A 8/1980 Willson
4,306,562 A 12/1981 Osborne
(Continued)

FOREIGN PATENT DOCUMENTS

EP 0801955 A1 10/1997
EP 0801955 B1 3/1999
(Continued)

*Primary Examiner* — Michael F Peffley
(74) *Attorney, Agent, or Firm* — Mueting, Raasch & Gebhardt, P.A.

(57) ABSTRACT

An improved system and method for placing implantable medical devices (IMDs) such as leads within the coronary sinus and branch veins is disclosed. In one embodiment, a slittable delivery sheath and a method of using the sheath are provided. The sheath includes a slittable hub, and a substantially straight body defining an inner lumen. The body comprises a shaft section and a distal section that is distal to, and softer than, the shaft section. A slittable braid extends adjacent to at least a portion of one of the shaft section and the distal section. In one embodiment of the invention, the sheath further includes a transition section that is distal to the shaft section, and proximal to the distal section. The transition section is softer than the shaft section, but stiffer than the distal section.

12 Claims, 16 Drawing Sheets

Related U.S. Application Data division of application No. 10/131,436, filed on Apr. 25, 2002, now Pat. No. 7,497,844, which is a continuation-in-part of application No. 09/822,678, filed on Mar. 30, 2001, now Pat. No. 6,743,227.

(60) Provisional application No. 60/193,695, filed on Mar. 31, 2000.

(51) Int. Cl.
| | |
|---|---|
| *A61B 18/14* | (2006.01) |
| *A61M 25/01* | (2006.01) |
| *A61N 1/05* | (2006.01) |
| *A61B 17/22* | (2006.01) |
| *A61M 25/10* | (2013.01) |
| *A61B 18/00* | (2006.01) |

(52) U.S. Cl.
CPC .... *A61M 25/0138* (2013.01); *A61M 25/0141* (2013.01); *A61M 25/0147* (2013.01); *A61N 1/056* (2013.01); *A61B 2017/22038* (2013.01); *A61B 2018/00386* (2013.01); *A61M 25/005* (2013.01); *A61M 25/0051* (2013.01); *A61M 25/0054* (2013.01); *A61M 2025/0042* (2013.01); *A61M 2025/0047* (2013.01); *A61M 2025/0081* (2013.01); *A61M 2025/0161* (2013.01); *A61M 2025/0681* (2013.01); *A61M 2025/1052* (2013.01); *A61M 2025/1079* (2013.01); *A61N 2001/0578* (2013.01); *A61N 2001/0585* (2013.01)

(58) Field of Classification Search
CPC .. A61M 2025/1079; A61M 2025/1052; A61M 2025/0042; A61M 2025/0161
See application file for complete search history.

(56) References Cited

U.S. PATENT DOCUMENTS

| | | | |
|---|---|---|---|
| 4,624,266 A | 11/1986 | Kane | |
| 4,813,434 A | 3/1989 | Buchbinder et al. | |
| 4,898,577 A * | 2/1990 | Badger | A61M 25/0152 604/528 |
| 4,911,148 A | 3/1990 | Sosnowski et al. | |
| 5,092,834 A | 3/1992 | Bradshaw et al. | |
| 5,167,634 A | 12/1992 | Corrigan, Jr. et al. | |
| 5,176,661 A | 1/1993 | Evard et al. | |
| 5,304,131 A | 4/1994 | Paskar | |
| 5,312,355 A | 5/1994 | Lee | |
| 5,320,613 A | 6/1994 | Houge et al. | |
| 5,441,483 A | 8/1995 | Avitall | |
| 5,501,694 A * | 3/1996 | Ressemann | A61B 17/320725 604/22 |
| 5,507,725 A | 4/1996 | Savage et al. | |
| 5,509,411 A | 4/1996 | Littmann et al. | |
| 5,562,619 A * | 10/1996 | Mirarchi | A61B 17/221 604/264 |
| 5,569,296 A | 10/1996 | Marin et al. | |
| 5,620,417 A | 4/1997 | Jang et al. | |
| 5,645,064 A | 7/1997 | Littmann et al. | |
| 5,645,082 A | 7/1997 | Sung et al. | |
| 5,682,885 A | 11/1997 | Littmann et al. | |
| 5,693,015 A | 12/1997 | Walker et al. | |
| 5,697,948 A | 12/1997 | Marin et al. | |
| 5,699,796 A | 12/1997 | Littmann et al. | |
| 5,701,298 A | 12/1997 | Diachina et al. | |
| 5,706,809 A | 1/1998 | Littmann et al. | |
| 5,711,298 A | 1/1998 | Littmann et al. | |
| 5,766,152 A | 6/1998 | Morley et al. | |
| 5,775,327 A * | 7/1998 | Randolph | A61M 25/0054 600/374 |
| 5,782,760 A | 7/1998 | Schaer | |
| 5,824,031 A | 10/1998 | Cookston et al. | |
| 5,827,278 A | 10/1998 | Webster, Jr. | |
| 5,827,296 A | 10/1998 | Morris et al. | |
| 5,836,925 A * | 11/1998 | Soltesz | A61L 29/14 604/264 |
| 5,855,560 A | 1/1999 | Idaomi et al. | |
| 5,863,291 A | 1/1999 | Schaer | |
| 5,868,768 A | 2/1999 | Wicherski et al. | |
| 5,881,732 A | 3/1999 | Sung et al. | |
| 5,882,333 A | 3/1999 | Schaer et al. | |
| 5,885,238 A | 3/1999 | Stevens et al. | |
| 5,902,289 A | 5/1999 | Swartz et al. | |
| 5,921,924 A | 7/1999 | Avitall | |
| 5,931,861 A | 8/1999 | Werner et al. | |
| 5,957,968 A | 9/1999 | Belden et al. | |
| 5,967,978 A | 10/1999 | Littmann et al. | |
| 5,999,858 A | 12/1999 | Sommer et al. | |
| 6,002,956 A | 12/1999 | Schaer | |
| 6,021,340 A | 2/2000 | Randolph et al. | |
| 6,122,552 A | 9/2000 | Tockman et al. | |
| 6,144,882 A | 11/2000 | Sommer et al. | |
| 6,156,018 A | 12/2000 | Hassett | |
| 6,159,198 A | 12/2000 | Gardeski et al. | |
| 6,192,280 B1 | 2/2001 | Sommer et al. | |
| 6,428,489 B1 | 8/2002 | Jacobsen et al. | |
| 6,733,500 B2 | 5/2004 | Kelley et al. | |
| 6,733,516 B2 | 5/2004 | Simons et al. | |
| 6,743,227 B2 | 6/2004 | Seraj et al. | |
| 6,836,687 B2 | 12/2004 | Kelley et al. | |
| 7,497,844 B2 | 3/2009 | Spear et al. | |
| 2001/0005783 A1 | 6/2001 | Hassett | |
| 2001/0044624 A1 | 11/2001 | Seraj et al. | |
| 2002/0165536 A1 | 11/2002 | Kelley et al. | |
| 2002/0165537 A1 | 11/2002 | Kelley et al. | |
| 2002/0173785 A1 | 11/2002 | Spear et al. | |

FOREIGN PATENT DOCUMENTS

| | | |
|---|---|---|
| EP | 1060757 A1 | 12/2000 |
| FR | 2804608 A1 | 8/2001 |
| FR | 2809016 A1 | 11/2001 |
| JP | 07-051381 | 2/1995 |
| WO | WO 01/02047 A1 | 1/2001 |
| WO | WO 2002/004062 A2 | 1/2002 |

* cited by examiner

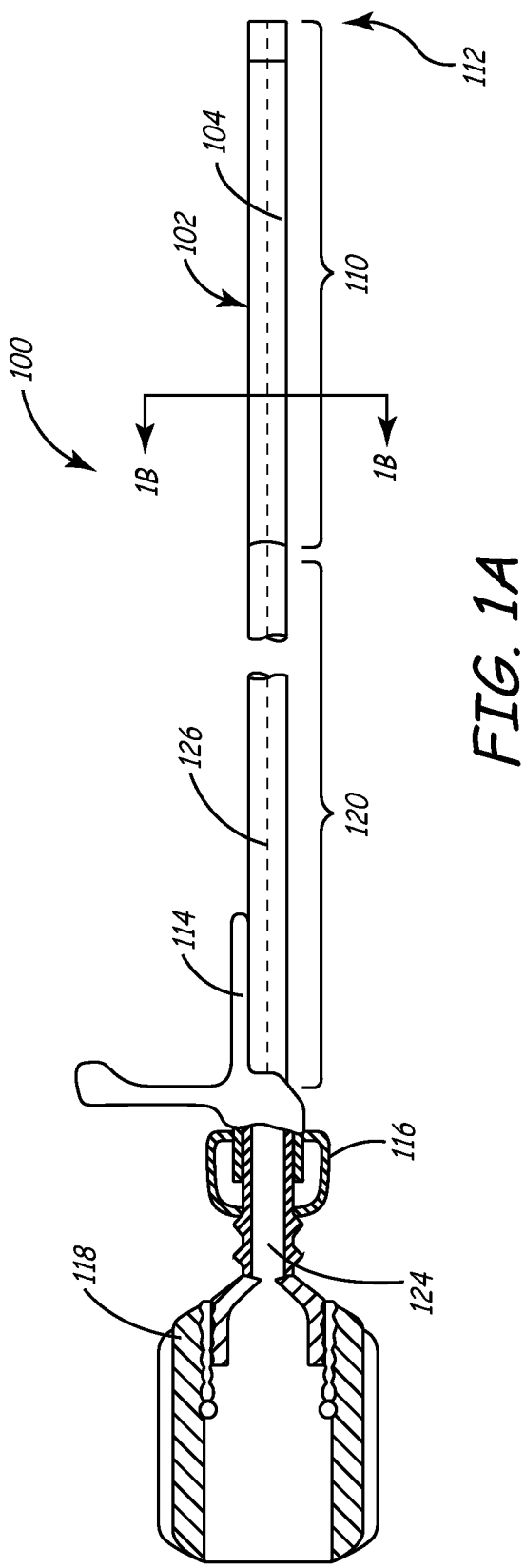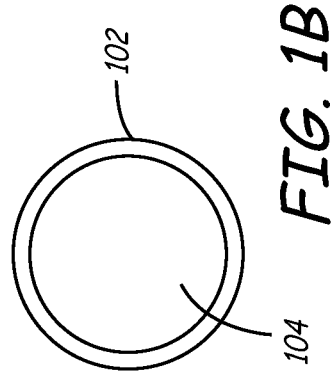

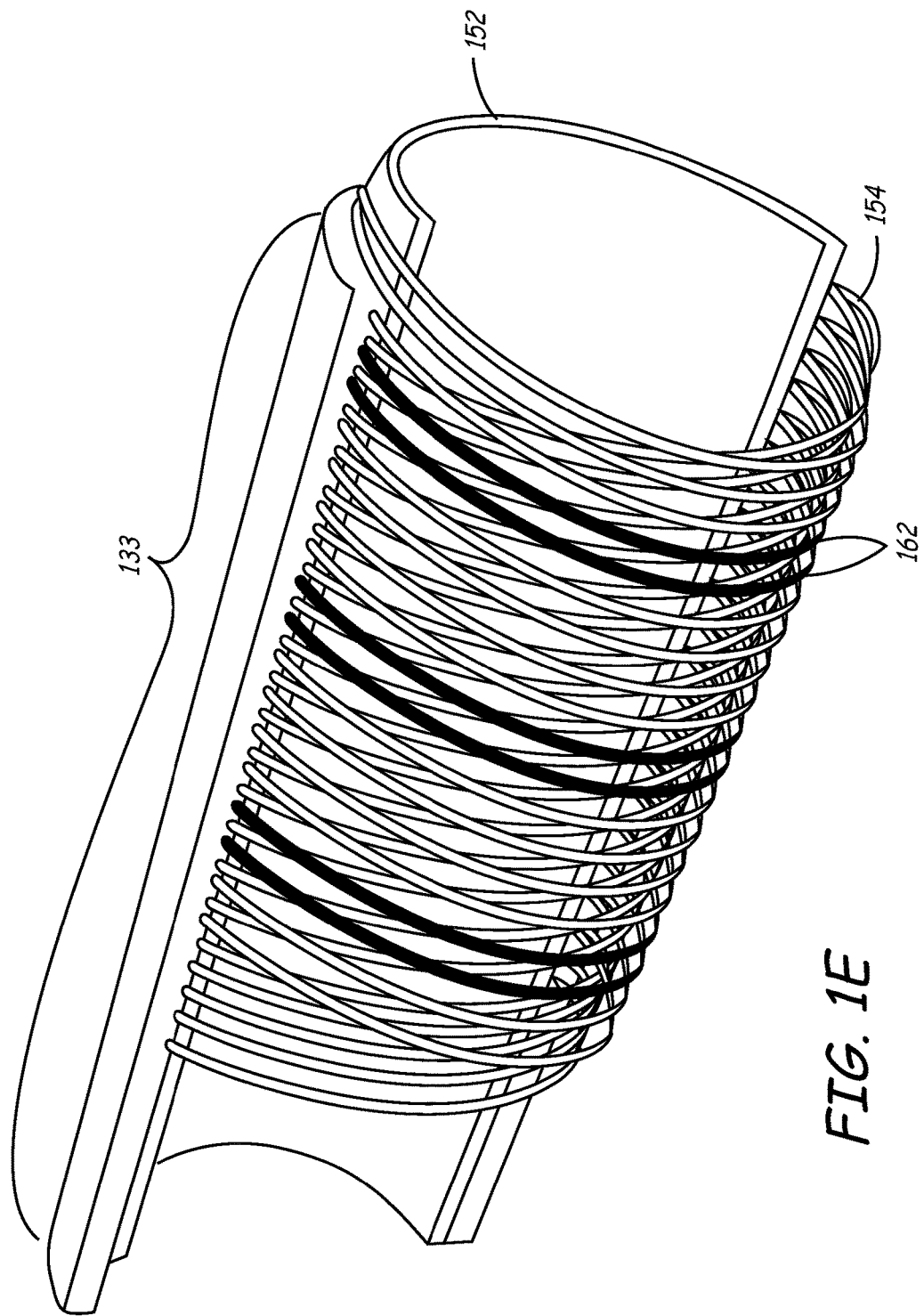

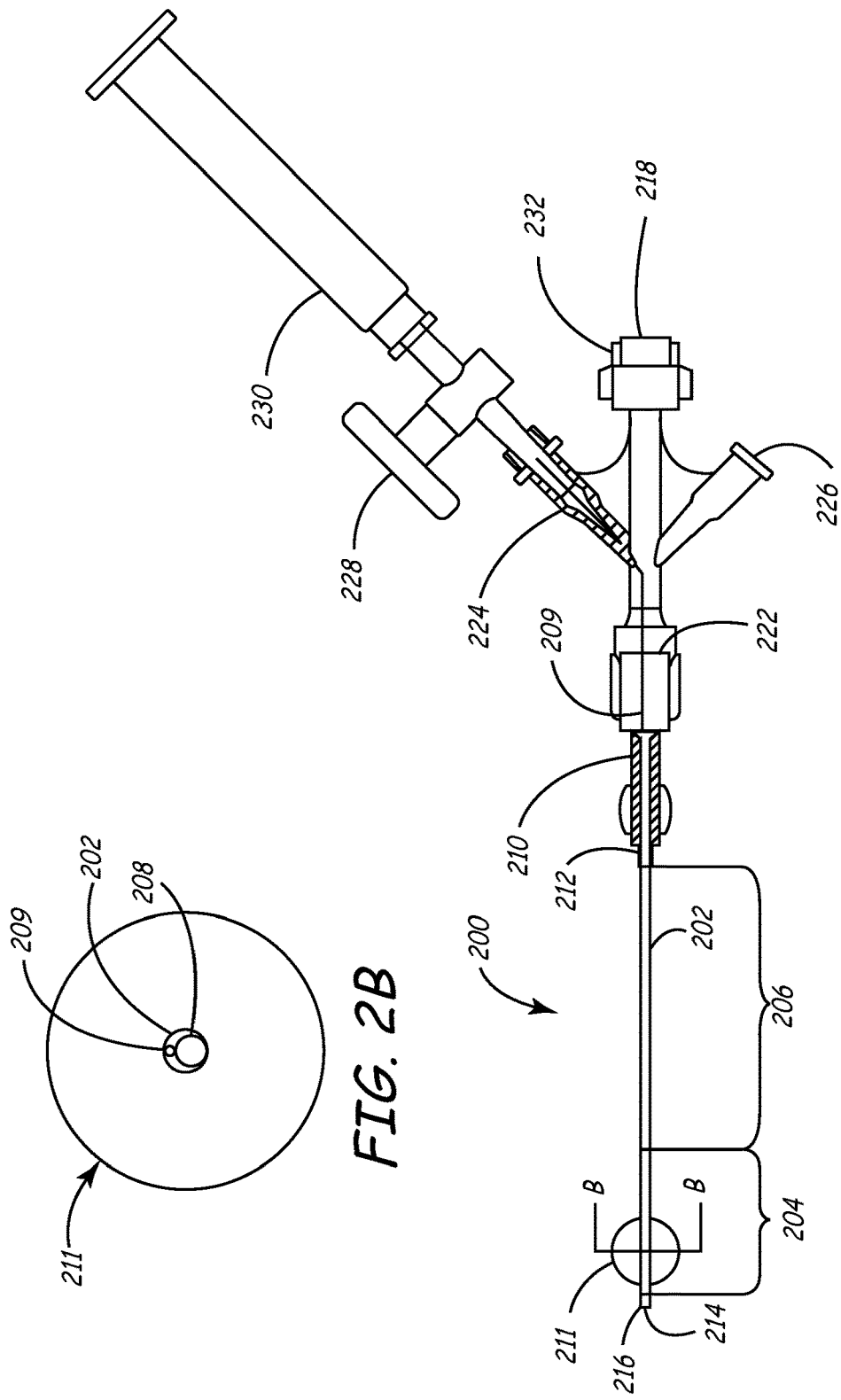

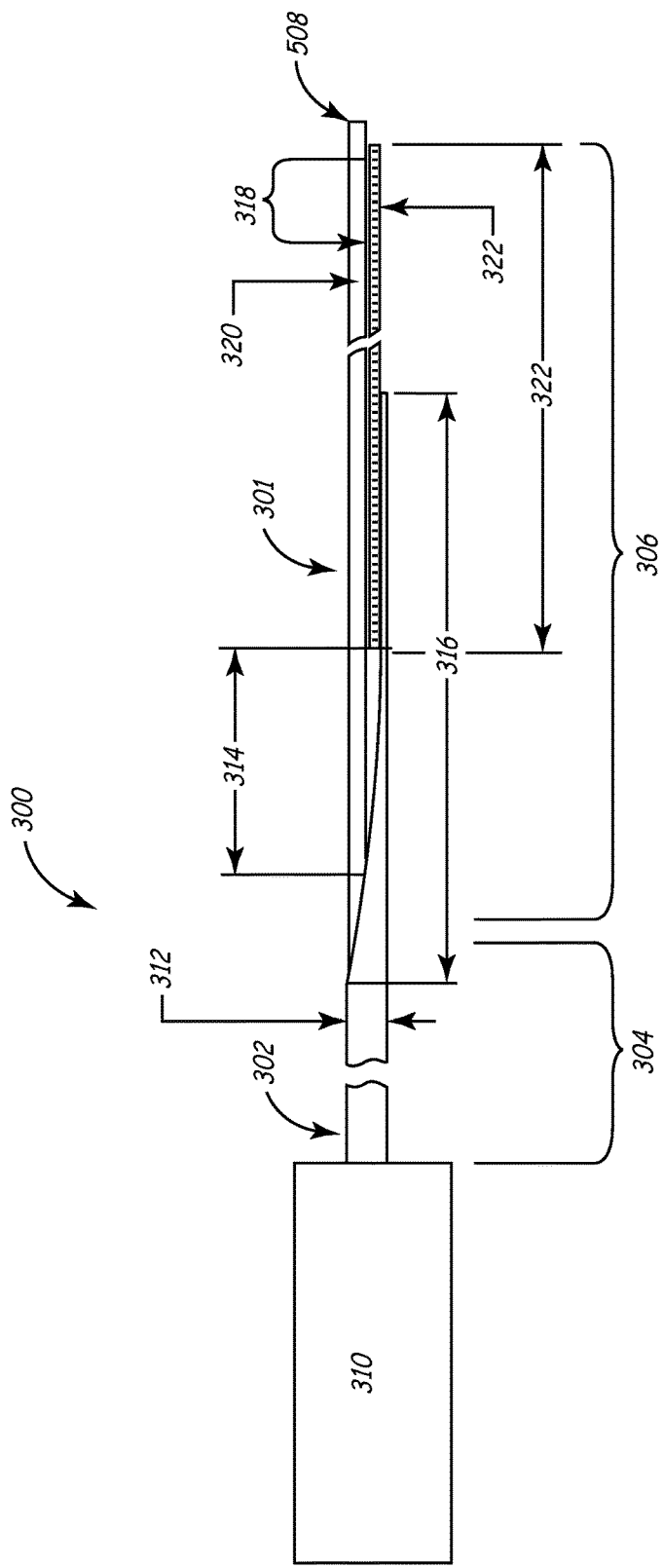

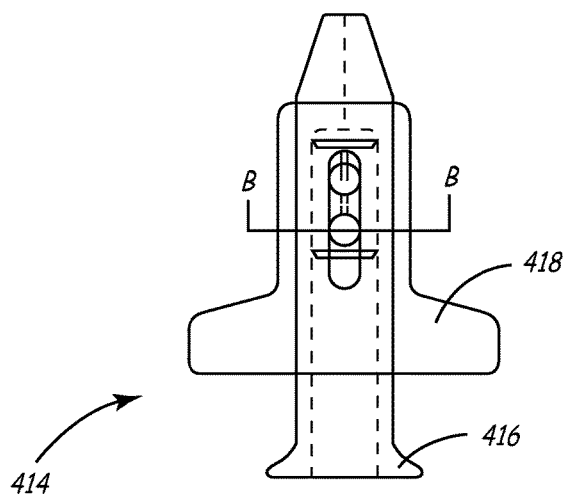
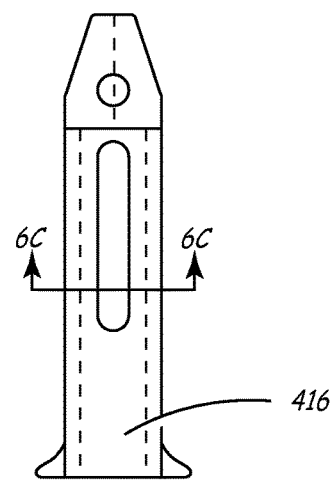
FIG. 6A  FIG. 6D
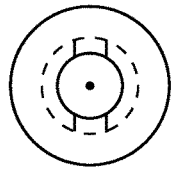
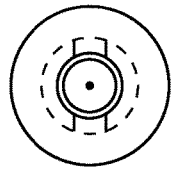
FIG. 6B  FIG. 6C

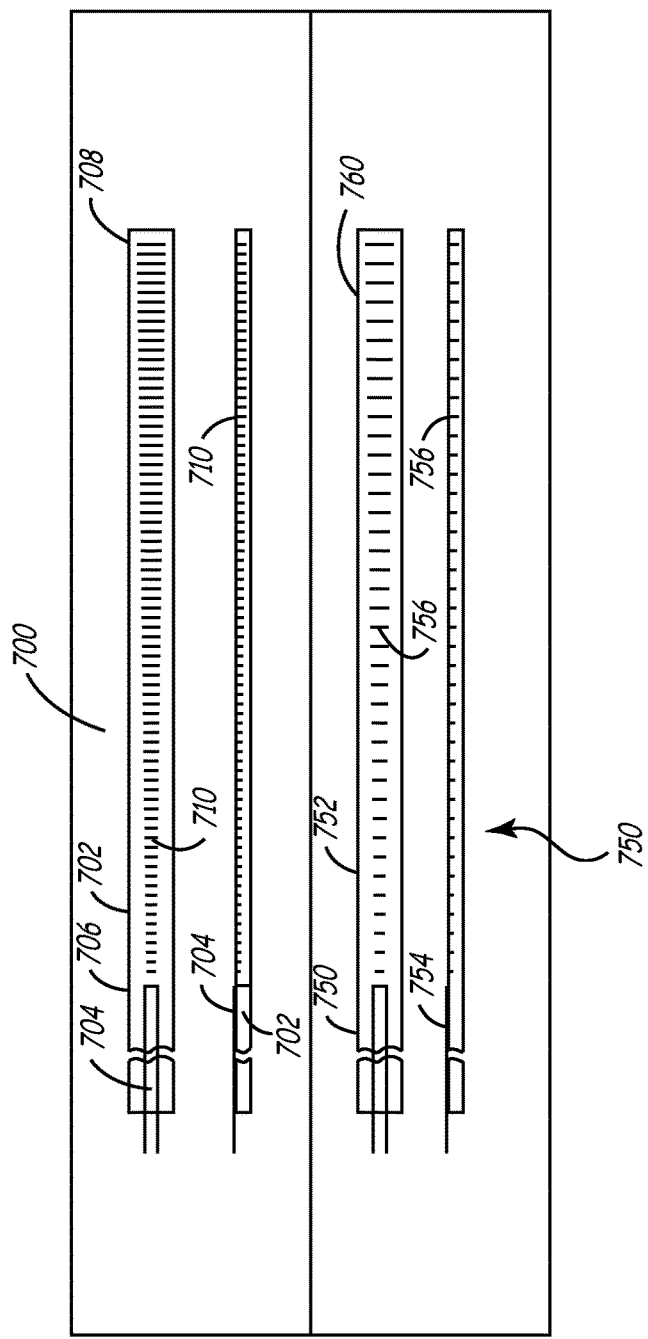

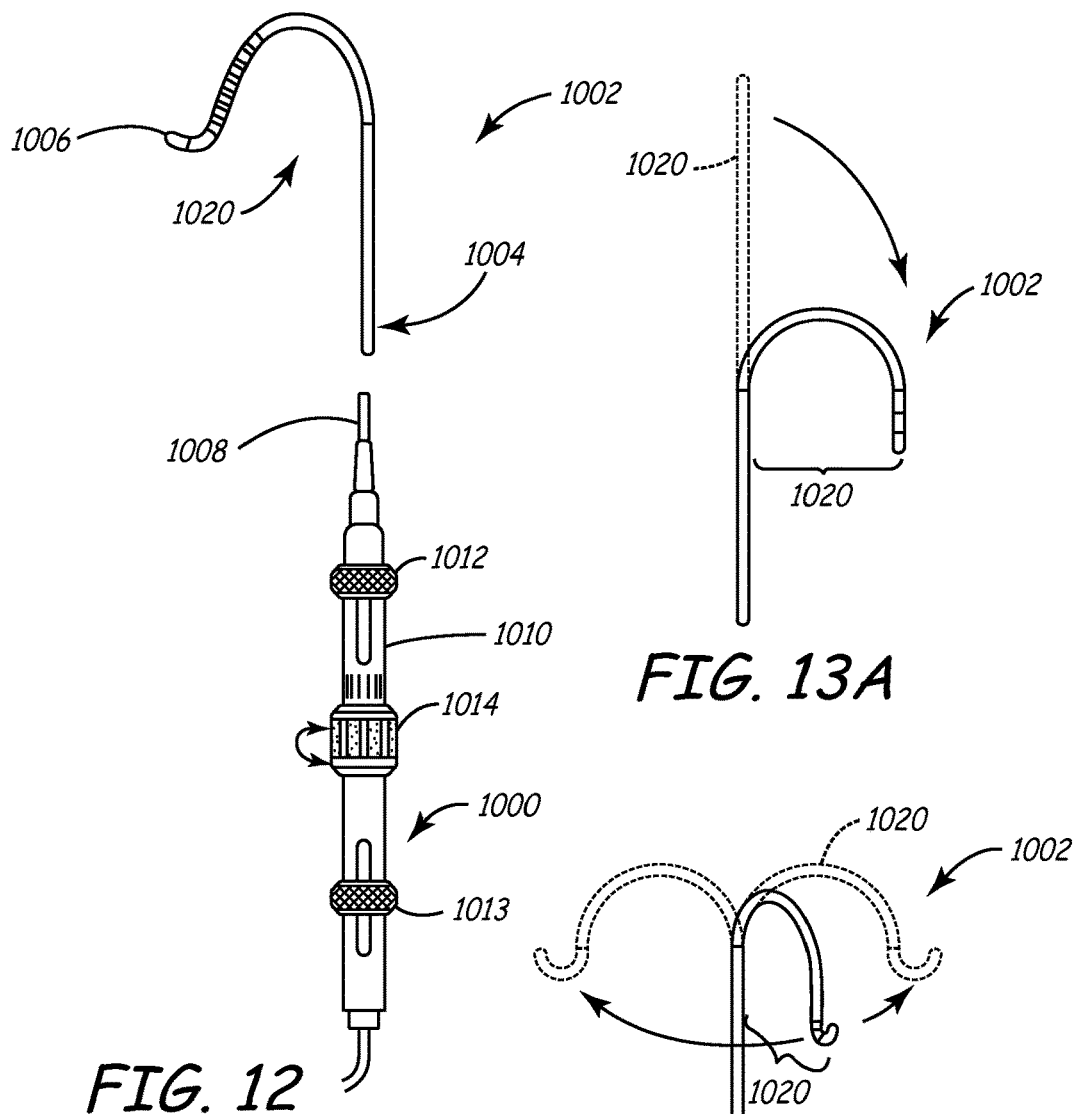
FIG. 12
FIG. 13A
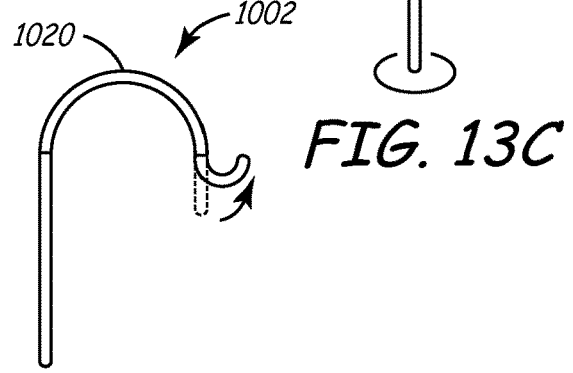
FIG. 13B
FIG. 13C

SYSTEM AND METHOD FOR POSITIONING IMPLANTABLE MEDICAL DEVICES WITHIN CORONARY VEINS

RELATED APPLICATION

This application is a continuation of U.S. patent application Ser. No. 12/357,810, filed Jan. 22, 2009 (now U.S. Pat. No. 8,734,397) entitled "IMPROVED SYSTEM AND METHOD FOR POSITIONING IMPLANTABLE MEDICAL DEVICES WITHIN CORONARY VEINS", herein incorporated by reference in its entirety, which is a divisional application of U.S. patent application Ser. No. 10/131,436, filed Apr. 25, 2002 (now U.S. Pat. No. 7,497,844), which is a continuation-in-part application of U.S. patent application Ser. No. 09/822,678, filed Mar. 30, 2001 (now U.S. Pat. No. 6,743,227), which claims the benefit of U.S. Provisional Patent Application Ser. No. 60/193,695, filed Mar. 31, 2000.

BACKGROUND OF THE INVENTION

This invention relates generally to a system and method for mammalian intralumenal visualization and delivery of various devices or agents into a targeted area of the body. More particularly, this invention relates to a visualization and delivery system for accurately placing devices such as leads, electrophysiology catheters, and therapeutic agents into large-organ vessel systems such as the coronary vasculature.

In treating conditions such as arrhythmia, one technique is to destroy or damage heart tissue that causes or is involved with the arrhythmia by suitably heating the tissue, e.g., by applying a laser beam or high-frequency electrical energy such as radio-frequency (RF) or microwave energy.

For such treatment to be effective, the location of the tissue site causing or involved with the arrhythmia must be accurately determined in order to be able to contact heart tissue adjacent the desired location with a tissue-destroying device. A high degree of accuracy in determining this site is paramount so that an excessive amount of viable tissue is not destroyed adjacent the site. For example, the average arrhythmogenic site consists of about 1.4 $cm^2$ of endocardial tissue, whereas a re-entrant site might be much larger. RF ablation techniques produce lesions about 0.5 $cm^2$ of diameter, so a number of lesions are typically generated in order to ablate the area of interest. If the site is not accurately mapped, much of the viable tissue surrounding the site will be unnecessarily destroyed.

To determine the location of the tissue to be ablated, it is widely known to use elongated intravascular signal sensing devices that are advanced through the patient's vasculature until the distal portions of the device are disposed within one or more of the patient's heart chambers, with one or more electrodes on the distal portion of the device in contact with the endocardial lining. Such devices may also be advanced within a patient's coronary artery, coronary sinus, or cardiac vein. Sensing devices such as those disclosed in U.S. Pat. No. 5,967,978 to Littmann et al., and combination sensing-ablation devices such as those disclosed in U.S. Pat. No. 6,002,956 to Schaer are typical.

Guiding catheters such as those disclosed in U.S. Pat. Nos. 6,021,340 and 5,775,327 to Randolph et al. may be used to rapidly advance such devices into a patient's cardiac vein draining into the coronary sinus. A particular advantage of the catheters disclosed in these references is the presence of an inner lumen and distal port on the catheter shaft, which, in conjunction with a distal balloon, allows for the deployment of contrast fluid distal to the distal end of the catheter for visualizing the venous structure.

The following U.S. patents discuss related devices and methods for their use: U.S. Pat. Nos. 5,509,411, 5,645,064, 5,682,885, 5,699,796, 5,706,809, and 5,711,298, each to Littmann et al; U.S. Pat. Nos. 5,881,732 and 5,645,082, each to Sung et al; U.S. Pat. No. 5,766,152 to Morely et al; U.S. Pat. Nos. 5,782,760 and 5,863,291, each to Schaer; U.S. Pat. No. 5,882,333 to Schaer et al., and U.S. Pat. No. 6,122,552 to Tockman et al.

However, despite the advantages of these sensing devices and guiding catheters, it remains quite difficult to accurately and reliably contact the various curved shapes one encounters in the endocardial lining. This is due to the frequent inability to customize the shape of their distal portion, or at least the inability to instantaneously and accurately adjust their shape upon demand during deployment to conform to the shape of the tissue of interest.

Concerns similar to those described above are associated with the placement of leads within the heart and other areas of the coronary vasculature. For example, pacemakers, defibrillator/cardioverters, and other implantable medical device (IMDs) may employ one or more electrodes that are maintained in contact with a patient's heart muscle and through which electrical stimulation of the heart muscle is achieved. Such devices typically employ a flexible conductive lead that connects a remotely positioned and implanted power source to the one or more electrodes. Secure placement of the electrodes in the selected heart chamber (typically the right atrium) or in a coronary vein or artery is required to assure appropriate and reliable depolarization or "capture" of cardiac tissue by electrical stimuli delivered by the IMD.

Many problems exist with reliably and accurately placing medical electrical leads and other similar devices such as catheters within the heart and associated vasculature. For instance, when placing transvenous leads or catheters, it is often difficult to engage the coronary sinus and sub-select the proper vessel into which the lead or catheter is to eventually be placed. Moreover, once placed, transvenous devices suffer from a relatively high rate of dislodgment from sites adjacent to, or on, the epicardium. Such dislodgement may result in a loss of capture or, at best, a reduction of the degree of electrical coupling between the electrode and the myocardium. More accurate and secure placement of the lead or catheter would not only reduce the difficulty and time associated with lead placement, but would reduce the risk of subsequent dislodgment as well.

There thus is a need for a method and system for placing intralumenally-deployed devices such as electrophysiology catheters and leads into selected areas of the coronary vasculature in a highly accurate and reliable fashion.

SUMMARY OF THE INVENTION

The current invention provides an improved system and method for placing implantable medical devices (IMDs) such as leads within the coronary sinus and branch veins. In one embodiment, a slittable delivery sheath is provided. The sheath includes a slittable hub, and a substantially straight body defining an inner lumen. The body comprises a shaft section and a distal section that is distal to, and softer than, the shaft section. A slittable braid extends adjacent to at least a portion of one of the shaft section and the distal section. In one embodiment of the invention, the sheath further includes a transition section that is distal to the shaft section, and proximal to the distal section. The transition section is softer than the shaft section, but stiffer than the distal section.

In one embodiment of the invention, at least one of the sections of the sheath includes multiple segments. In general, the stiffness associated with the multiple segments within a section decreases from the proximal to distal end of the section. For example, in one embodiment, the shaft section includes proximal, intermediate, and distal shaft segments, with the proximal shaft segment being the hardest, the intermediate shaft segment being more flexible, and the distal shaft section being the most flexible within the shaft section. Similarly, the transition section may include at least two segments, with the more proximal transition segment being harder than the distal transition segment. Finally, distal section includes a very soft atraumatic tip, and a soft distal segment. A harder intermediate segment may be provided between soft tip and soft distal segment to terminate the braid.

In one embodiment, the inner lumen of the sheath is between 0.086 and 0.106 inches, and in a particular embodiment is approximately 0.096 inches. The sheath may further include an internal liner adjacent to at least a portion of the inner lumen. This liner may be formed of a lubricious material such as PTFE to allow leads and other devices to be more easily advanced within the lumen.

The sheath of the current invention includes characteristics that make it ideal for placing leads and other devices within the coronary sinus or the branch veins thereof. For example, the segments at the distal end of sheath are formed of a relatively soft material, and therefore provide a very soft atraumatic tip that minimizes the chance of tissue damage. Additionally, the braid provides support to sheath shaft, making it more kink resistant as it is pushed through the vascular system during an implant procedure. Kink resistance is further enhanced by using the transition section to provide gradual changes between the stiffer shaft section and the soft distal section. As a result, the sheath can survive a ninety-degree bend without kinking when supported by another device such as a steerable EP catheter. These same attributes provide for a sheath that is more pushable than prior art designs, make it easier to navigate the torturous curves of the venous system.

The foregoing attributes also provide a device that is easier to remove from the body after a lead or other IMD has been positioned at a final implant location. The soft distal section and substantially straight profile of the sheath allow it to easily track over another device such as a lead to prevent the "whipping" effect that is commonly exhibited by prior art sheaths. This is particularly important when the sheath is withdrawn from the coronary sinus or branch vein, since a whipping motion can dislodge the lead, making it necessary to repeat the entire procedure.

Additionally, the sheath of the current invention is designed to be slittable. That is, the system uses braid materials that are slittable, yet provide maximum backup support and pushability to the sheath body. This allows the sheath to be slit away from leads and other IMDs having larger connectors, including IS-1 standard connectors. The selection of braid materials maintains this slitting capability without sacrificing the beneficial properties that make the sheath easier to navigate.

Finally, the sheath has an outer diameter that is small enough to be advanced within the coronary sinus and into branch veins. The very soft atraumatic tip allows this to be accomplished without damaging tissue. Additionally, the lubricious internal PTFE liner allows leads and other IMDs to be advanced within the sheath internal lumen when only a minimal amount of clearance is available.

According to yet another aspect of the invention, a system for positioning implantable medical devices within the coronary sinus or a branch vein is disclosed. The system includes an inventive sheath similar to that set forth above. The sheath is slittable, and has a substantially straight profile. The sheath further includes a shaft section, and a distal section that is distal to, and softer than, the shaft section. A slittable braid is provided adjacent to at least a portion of at least one of the shaft section and the distal section. The system further includes a steerable catheter having a shaft adapted to be inserted within the inner lumen of the sheath. The steerable catheter may be used to navigate the sheath into the coronary sinus and/or a branch vein thereof.

In still another embodiment of the invention, a method of using the novel sheath for seating implantable medical devices such as leads within the coronary sinus or branch veins is disclosed. The method includes providing a slittable sheath having a substantially straight body defining an inner lumen. The body of the sheath comprises a shaft section and a distal section that is distal to, and softer than, the shaft section. A slittable braid extends adjacent to at least a portion of one of the shaft section and the distal section. The method further includes inserting a steerable catheter such as a steerable EP catheter within the inner lumen of the sheath, positioning the steerable catheter and sheath within a body, and navigating the steerable catheter and the sheath into the coronary sinus of the body.

In one embodiment of the invention, the method further includes advancing an implantable medical device (IMD) such as a lead within the inner lumen of the sheath. The lead may be loaded with a navigational device prior to advancing the lead within the inner lumen of the sheath. Alternatively, a navigational device may be advanced within the lumen of the sheath, and the lead may be advanced over the navigational device. This navigational device may be a stylet, a guidewire, a micro-deflection mechanism, or any other navigational device known in the art. The lead and navigational device may then be used to sub-select a branch vein of the coronary sinus. In yet another embodiment, the sheath may sub-select the branch vein prior to advancing the lead and navigational device to a target destination.

Other scopes and aspects of the current invention will be apparent from the following description and the accompanying drawings.

BRIEF DESCRIPTION OF THE DRAWINGS

FIG. 1A is a side cutaway view of a delivery sheath of the present invention.

FIG. 1B is a cross-sectional view of a delivery sheath of the present invention.

FIG. 1E is a perspective cutaway view of the sheath of FIGS. 1C and 1D.

FIGS. 2A-2B are side and cross-sectional views, respectively, of a balloon catheter as may be used with the sheath of the present invention.

FIG. 3 is as side view illustrating components included in both the deflection mechanism and micro-deflection mechanism as may be used with the sheath of the present invention.

FIGS. 6A-6D are various views of a micro-deflection mechanism handle.

FIGS. 7A-7B are two embodiments of deflection and micro-deflection mechanisms detailing two notch configurations.

FIG. 12 is a plan view of a steerable catheter that may be used as an alternative deflection mechanism to navigate the balloon catheter 200 into the coronary sinus.

FIGS. 13A through 13C are side views of steerable catheter being deflected in various configurations.

DETAILED DESCRIPTION OF THE INVENTION

Figure 1C:
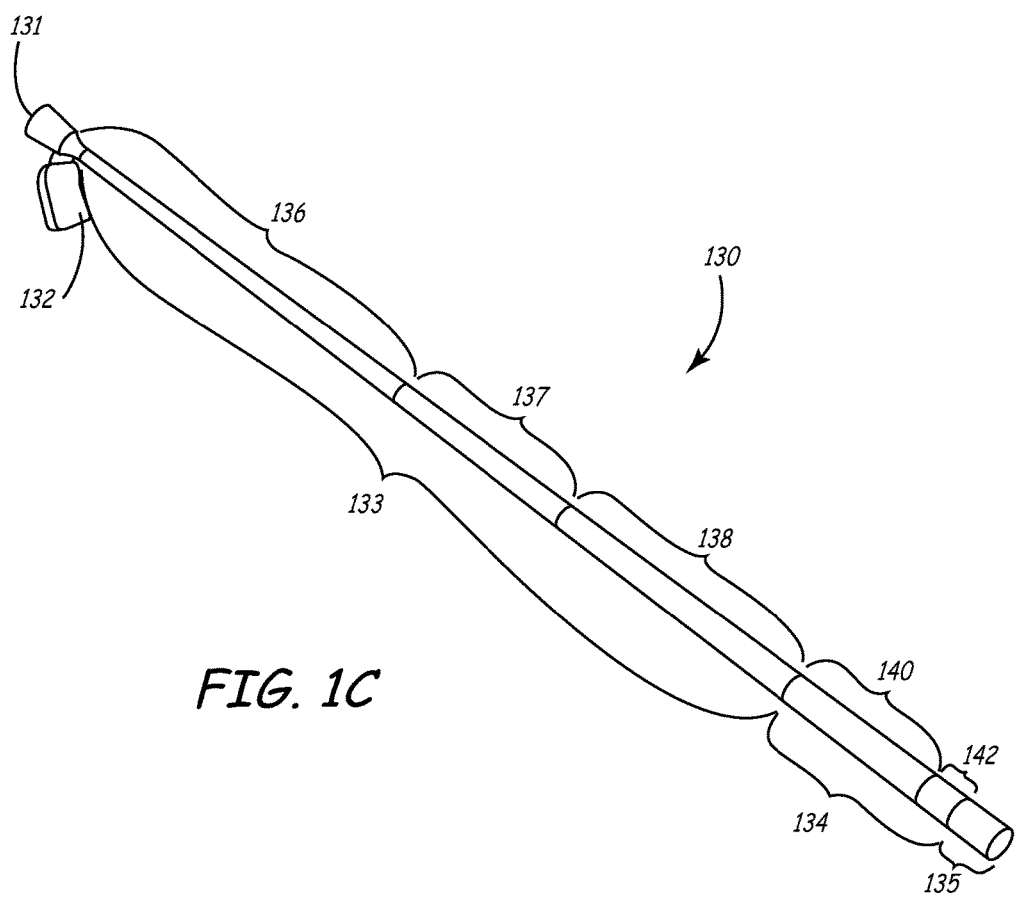
FIG. 1C is a perspective view of an additional embodiment of the sheath of the current invention.

This invention involves a method and system for intralumenal visualization and deployment of implantable medical devices (IMDs) such as transvenous leads, electrophysiology catheters and the like to various targeted regions of the body. The inventive system includes a sheath, which may be used along with a balloon catheter and associated deflection mechanism, and a micro-deflection device for highly accurate placement of the lead, catheter, or other device once the area of interest has been visualized.

The following description sets forth several embodiments of the inventive sheath, followed by a description of additional components that may be used with the sheath to place a transvenous lead into the coronary veins. Although the description sets forth several methods for using the sheath, as well as an exemplary set of system components for use in conjunction with the current invention, other system configurations, adaptations, and methods of use are within the scope of the invention.

In general, the invention involves a sheath that is adapted to be highly pushable, and yet having a soft enough distal tip to track a lead body or the body of another implantable medical device (IMD). The sheath may be positioned within a chamber of the heart or within a coronary vein such as the coronary sinus using a catheter such as a steerable electrophysiology (EP) catheter. The sheath may then be used to deploy an intralumenal visualization system and micro-deflection device that may include a deflectable catheter having an inflatable member such as a balloon. The inventive device may be inserted into the body via a typical introducer as will be described in more detail.

In one use of the sheath, the sheath and a steerable electrophysiology (EP) catheter are inserted together into the body. The EP catheter is employed to navigate the sheath into the coronary sinus. The EP catheter is withdrawn, and a balloon catheter is inserted into the lumen of the sheath so that a venogram may be obtained. The balloon catheter is withdrawn, a lead is inserted through the sheath lumen and into the coronary sinus. Using the venogram data, the lead may be advanced into a branch vein of the coronary sinus.

Because the sheath of the current invention has a body with a high degree of pushability and an extremely soft distal tip, it may be guided into a branch vein to aid in placement of the lead, if necessary. Once the lead is in position, the sheath may be withdrawn from the body. This can be accomplished by pulling the sheath in a proximal direction over the lead body and connector. Since the sheath is substantially straight and possesses a very flexible, soft distal tip, the sheath body tracks the lead as it is withdrawn from the coronary sinus during this process. This prevents a "whipping" effect that may cause lead dislodgment. The current sheath is further designed to be slittable, so that it may be removed from a lead having a standard, larger profile, connector such as an IS-1 connector.

In another variation of the above-described process, a balloon catheter is guided by a deflection mechanism to engage the coronary sinus ostium, and an occlusive venogram is obtained. The sheath of the current invention is then slid over the balloon catheter into the coronary sinus, and the balloon catheter is removed. A lead with a micro-deflection mechanism is inserted into the sheath lumen and is deployed at a desired location in the coronary veins. The micro-deflection mechanism disposed within the lead is used to provide rigidity to the lead and to allow a means to sub-select coronary vessels. As described above, the sheath may be splittable along its longitudinal length so that it may be removed around the lead without disturbing it. With the foregoing system summary set forth as background information, a detailed description of the inventive sheath follows.

Delivery Sheath

FIG. 1A is a cutaway side view depicting one embodiment of the delivery sheath of the current invention. As best seen in FIG. 1A, sheath 100 comprises an elongate shaft 102 containing a central lumen 104 throughout its length. The working length of sheath 100 comprises a distal end 112, a distal section 110, and a proximal section 120, each of which comprises a polymeric jacket material having differing flexibilities as described below.

Near the proximal end of sheath 100, a hub 114 may be affixed to proximal section 120 by an adhesive or other suitable means. An ultraviolet-curable adhesive sold by Loctite Corp. of Rocky Hill, Conn. under the name UV 4201 may be used for this purpose. Alternatively, an adhesive sold by Dymax corp. of Trorrington, Conn. under the trademark DYMAX may be employed. Hub 114 is made from any suitable medical-grade polymer, and is preferably injection molded and longitudinally scored or perforated so that it may be removed from around a device without disturbing that device. It may be molded in situ onto the proximal section 120 of shaft 102.

In one embodiment, hub 114 has an opening large enough to accommodate a special rotatable hemostatic valve (RHV) 118, which seals a compressible annular ring on valve 118 inner diameter. A central lumen 124 in RHV 118 is aligned and in fluid communication with the lumen of shaft 102. Lumen 124 has a diameter large enough to accommodate a balloon catheter and a typical lead connector, such as an IS-1-type connector. An optional side arm (not shown) may be disposed on RHV 118 in fluid communication with lumen 124. RHV 118 may also be splittable via a scoring or perforation as described above.

An annular polymeric collar 116 is disposed on the outside diameter of RHV 118 distal portion proximal to the point where hub 114 meets RHV 118. In this embodiment, rotation of collar 116 locks the RHV 118 to hub 114. Hub 114 may have a non-standard diameter so that RHV 118 can be removed over an IS-1 lead connector prior to slittably removing sheath 100 from the lead.

FIG. 1B is a cross-sectional view of the delivery sheath embodiment of FIG. 1A. As shown in FIG. 1B, a cross-section of shaft 102 in the distal section 110 reveals shaft lumen 104. The inner diameter of shaft 102 will vary depending on the outer diameter of the balloon catheter and the lead, each of which should be capable of passing through lumen 104. Typically the shaft inner diameter is between about 0.070 and 0.110 inches. In one embodiment, the shaft inner diameter is between about 0.096 and 0.098 inches. Likewise, in one embodiment, the outer diameter of shaft 102 is between about 0.090 and 0.140 inches, and may be between 0.116 and 0.118 inches. It is desirable to make the outer diameter of shaft 102 as small as possible while still maintaining acceptable performance levels according to the application for which the shaft is used. Additionally, it is desirable for shaft 102 to maintains a substantially constant inner diameter throughout its length to provide a smooth and continuous step-free profile for the passage of various devices and materials therethrough as described herein.

Tubing comprising distal section 110 and proximal section 120 will typically be polymeric, and is preferably any typical acute-use medical grade, biocompatible tubing with the appropriate performance characteristics as described herein. An especially desirable material is an extruded polyether block amide of the type sold by Atochem North America, Inc., Philadelphia, Pa. under the trademark PEBAX.

In the current embodiment, distal and proximal sections 110 and 120, respectively, are constructed of tubing having a durometer hardness ranging from about 20 D to 100 D (shore). The working length of shaft 102 preferably is composed of materials having two or more stiffnesses, although shaft 102, having a single stiffness value throughout its length is within the scope of the invention. In the latter embodiment, Grilamid ELY 2702 from EMS Chemie may be employed to form a single-stiffness shaft 102. In either case, the shaft may have an inner diameter of about 0.098 inches, and an outer diameter of about 0.136 inches.

In one embodiment, proximal section 120 comprises a relatively high stiffness material (typically about 72 D) in comparison to the more flexible distal section 110 (typically about 40 D). Although not shown in the view of FIG. 1B, distal section 110 and proximal section 120 may be comprised of a DACRON polyester (E.I. du Pont de Nemours and Company, Wilmington, Del.) braid with a PolyTetra-FluoroEthylene (PTFE) liner. It may be noted that incorporation of this type of polyester braid within sheath 100 results in a structure that is less stiff than if a stainless steel braid is used, as is described below in reference to another embodiment of sheath 100. The braid may be surrounded by the PEBAX tubing, which renders the proximal section 120 of shaft 102 generally stiffer and less flexible than distal portion 110.

Distal end 112 is preferably a soft, atraumatic tip made from a relatively low stiffness polymeric material to prevent injury to the intima of the vessel walls or to other tissue. One material well suited for distal end 112 is a low-durometer thermoplastic polyurethane elastomer such as PELLETHANE (Dow Chemical Co., Midland, Mich.) or the like.

According to one aspect of the invention, distal portion 110 may be radiopaque. This can be achieved by the inclusion of radiopaque metals or their alloys into the structure, or more preferably by incorporating radiopaque filler materials such as $BaSO_4$, $BiCO$, etc. into the polymer comprising distal portion 110. Distal end 112 is preferably more radiopaque than distal portion 110. This can be achieved by the incorporation of greater quantities of radiopaque materials, for instance, into the tubing, or by the use of a different material having greater radiopacity than that used in distal portion 110. This radiopaque feature allows the user to more readily visualize these portions of sheath 100 under fluoroscopy.

The entire length of shaft 102 (from distal end 112 to the far proximal end of RHV 118) is typically between about 40 and 60 cm, and in the current embodiment is about 55 cm. Distal end 112 may be between about 0.2 cm and 0.5 cm long, while distal section 110 is generally between about 5 and 10 cm long, and is preferably about 8 cm long. Proximal section 120 is between about 35 and 50 cm long, and in the current embodiment is approximately 42 cm.

Both the working length of shaft 102 as well as the attached hub 114 may contain a perforation or score 126 along their longitudinal axes. Alternatively, they may be otherwise configured to split so that they may be opened and removed from around an inserted device such as a lead or electrophysiology catheter without having to axially slide the sheath 100 relative to the device. A special tool may be used to facilitate such splitting, or the sheath/hub (and even RHV 118) combination may be split by hand without the aid of any special device. The splittable valve and sheath combinations as described in U.S. Pat. No. 5,312,355 to Lee is exemplary.

In another embodiment, the materials included within sheath 100 may be selected so that the sheath is slittable. For example, the braid materials included within sheath are of a thickness that may be severed with currently-available slitting tools. A slitting tool of the type that may be used to remove a sheath of this embodiment is described in commonly-assigned U.S. patent application Ser. No. 10/078,026 filed Feb. 15, 2002 entitled "Slitting Tool". This is discussed further below in regards to the following additional embodiment.

FIG. 1C is a perspective view of an additional embodiment of the sheath of the current invention. At the proximal end, sheath 130 includes a hub 131 that is shown coupled to handle 132. Handle 132 may be integrally formed with hub, or may be coupled to hub by any coupling mechanism known in the art. Hub is formed of a material that is soft enough to be slittable using conventional sitting tools of the type described in the above-referenced application entitled "Slitting Tool". In one embodiment, hub 131 is formed of PEBAX having a durometer hardness of 70 D (Shore).

The body of sheath 130 includes multiple sections, each having an outer polymer layer, which may be formed of PEBAX tubing. The hardness of the polymer in each section generally decreases from the proximal to the distal end of sheath 130. In this embodiment, proximal end of sheath 130 includes a shaft section 133 that has a length ranging from about 43 to about 62 cm and a hardness that may range from about 72 D to 55 D. Distal to shaft section 133 is a transition section 134 having a length of between approximately 2.25 and 5.5 cm, and having a hardness ranging from approximately 35 D to 40 D. Finally, shaft includes a distal section 135 distal to transition section 134. Distal section 135 has a length of approximately 1.5 to 3.5 cm, and a hardness that is less than transition section 134, and which may range from 25 D to 35 D.

According to one embodiment of the current invention, shaft section 133 may be sub-divided into segments. In FIG. 1C, shaft section 133 includes three segments 136, 137, and 138 of varying hardnesses. For example, proximal shaft segment 136 may have a length that ranges from 40 to 55 cm, and a hardness that ranges from 70 D to 72D (Shore). In one particular embodiment, proximal shaft segment 136 has a length of between 45 and 50 cm, and hardness of approximately 72 D.

In the current embodiment, shaft section 133 next includes an intermediate shaft segment 137 having a length that ranges from approximately 1.5 to 3.5 cm, and a hardness that ranges from 63 D to 72 D. The particular embodiment includes intermediate shaft segment 137 having a length of approximately 2.5 cm, and a hardness of approximately 63 D. Finally, distal shaft segment 138 has a length of between approximately 1.5 to 3.5 cm, and a hardness that ranges from 55D to 63 D. The particular embodiment includes distal shaft segment 138 that is between 2 and 3 cm, and preferably 2.5 cm, in length, and which has a hardness of approximately 55 D.

In a manner similar to that discussed above with respect to shaft section 133, transition section 134 may be sub-divided into segments. For example, FIG. 1C illustrates transition section 134 including proximal transition segment 140 and distal transition segment 142. Proximal transition segment 140 has a length ranging between approximately 1.5 to 3.5 cm, and a hardness that ranges from 35 D to 40 D. In the particular embodiment, proximal transition segment 140 is between 2 and 3 cm, and preferably 2.5 cm, long. In this particular embodiment, proximal transition segment 140 has a hardness of approximately 40 D. Distal transition segment 142 has a length ranging between 0.75 and 2.0 cm, and a hardness ranging between 35 D to 40 D. In the particular embodiment, distal transition segment 142 is between approximately 1 to 2 cm, and preferably about 1.25 cm, in length. The hardness of distal transition segment 142 in the particular embodiment is approximately 35 D.

In a manner similar to that described above with respect to shaft section 133 and transition section 134, distal section 135 may include multiple segments (not shown in FIG. 1C). This is discussed further below.

Each of sections 133, 134, and 135 of shaft may incorporate radiopaque filler material such as BaSO$_4$ into the polymer jacket to make sheath 130 visible under a fluoroscope. In one embodiment, the PEBAX of shaft section 133 is approximately 30% BaSO$_4$ by weight. Similarly, transition section 134 includes between 30% and 40% BaSO$_4$ by weight. In one embodiment, proximal transition segment 140 is approximately 30%, and distal transition segment 142 is about 40%, BaSO$_4$ by weight. This allows the distal tip section to be slightly more visible than the more proximal section under flouroscope. Similarly, distal section may be between approximately 30% and 40% BaSO$_4$ by weight. Distal section may further be loaded with tungsten carbide to make it even more radiopaque.

In one embodiment, distal section includes a radiopaque marker band. The radiopaque marker band may be formed by loading a portion of the polymer jacket with an even higher percentage of a radiopaque filler material, or by incorporating a filament of metal having a high radiodensity, such as gold or platinum, within the distal section.

Figure 1D:
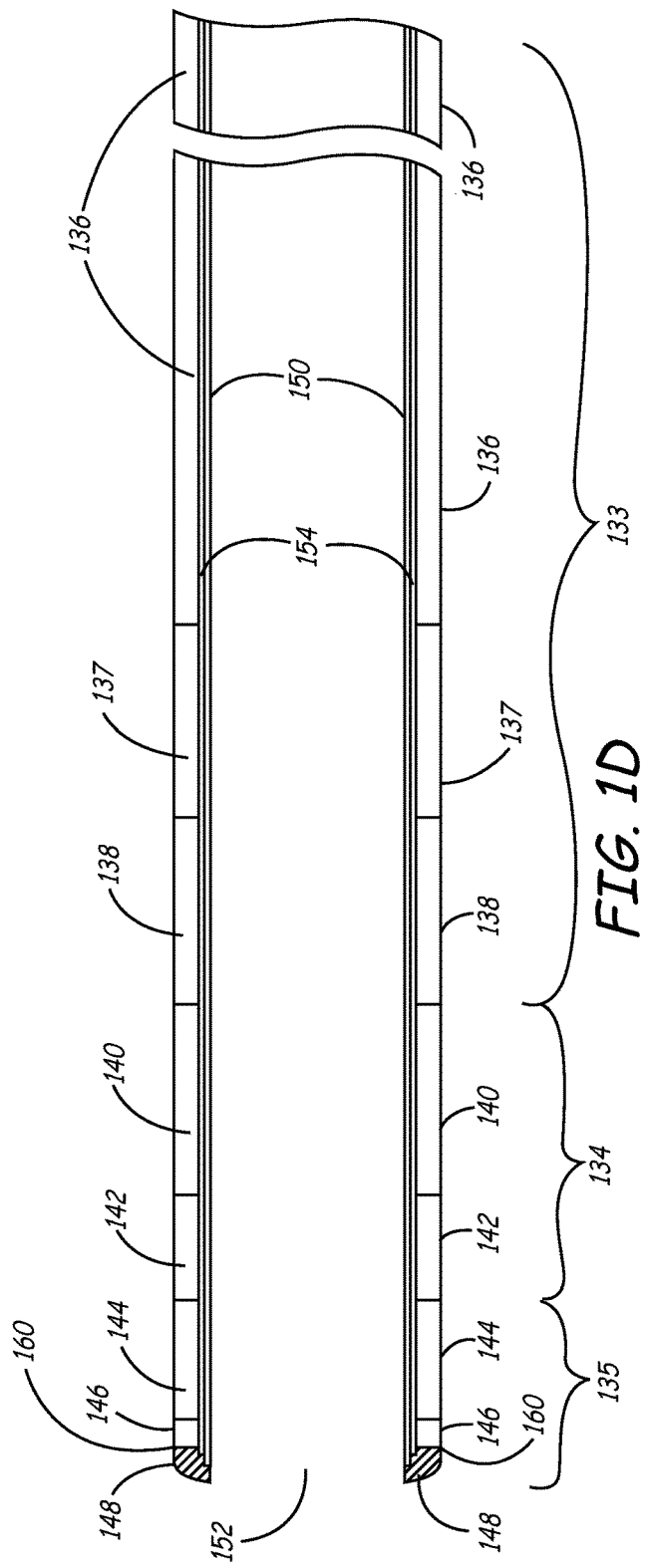
FIG. 1D is a side cut-away view of the sheath shown in FIG. 1C.

FIG. 1D is a side cut-away view of the sheath embodiment shown in FIG. 1C. FIG. 1D includes shaft section 133, transition section 134, and distal section 135. As noted above, shaft section 133 is divided into segments 136, 137, and 138, and transition section 134 is divided in segments 140 and 142. Similarly, distal section 135 may also be divided into portions shown as a soft distal segment 144, an intermediate distal segment 146, and a soft tip 148. Soft tip 148 is between 0.15 and 0.35 cm long, and in the particular embodiment is approximately 0.25 cm long. Soft tip is made of material that is very soft to prevent tissue damage. In one embodiment, soft tip 148 is formed of PEBAX with a hardness ranging from 25 D to 35 D, and is preferably 25 D PEBAX. Soft tip 148 may extend slightly beyond internal liner 150, as shown in FIG. 1D. Additionally, soft tip 148 may be radiused such that the distal end of sheath 130 has a rounded profile that will reduce chance of tissue perforation.

For reasons discussed below, a harder intermediate distal segment 146 may be provided just proximal to soft tip 148. Intermediate distal segment 146 may have a length of between about 0.2 and 0.45 cm, and in the particular embodiment, is approximately 0.37 cm in length. This segment may be formed of PEBAX having a hardness ranging from 35 D to 72 D, and is preferably 35 D PEBAX. According to one aspect of the invention, intermediate distal segment 146 comprises a radiopaque marker band that is visible under a fluoroscope. This radiopaque marker band may take the form of any of the embodiments discussed above.

Finally, soft distal segment 144 is formed of a material having a hardness that is similar to that used to form soft tip 148. Soft distal segment 144 may be between about 1 and 3 cm, and in the particular embodiment is approximately 1.9 cm.

The current embodiment of sheath 130 has an internal lumen 152 having an inner diameter that may range from approximately 0.086 to 0.106 inches, and in a particular embodiment, has an inner diameter of about 0.096 inches. The surface of lumen 152 is provided by an internal liner 150 extending along at least part of the length of lumen 152. This liner may be formed of a lubricious material such as PTFE, PolyVinylDieneFluoride (PVDF), or High-Density PolyEthylene (HDPE) to allow IMDs such as leads to be easily slid within the lumen. In an embodiment that does not include liner 150, the surface of lumen 152 may be coated with a hydrophilac material to make that surface more lubricious.

Sheath 130 of the current embodiment may further include a braided reinforcement such as braid 154 extending along at least a portion of at least one of the sections of sheath 130. This braid may be constructed of any biocompatible metal such as stainless steel. In the current embodiment, braid 154 is formed of 0.002-inch type-304 vacuum melt stainless steel wire. The wire may have a nominal Ultimate Tensile Strength (UTS) of between 200-250 kilopounds per square inch (ksi), and in the particular embodiment has a UTS of 220 ksi. The braid may include a continuous braid pattern such as eight wires by eight wires. In this particular embodiment, the braid configuration is further defined as having between 35 and 55 pic crossings (pics) per inch.

Braid 154 may optionally be terminated at its distal end using a heat shrink tube such polyester tubing. Alternately, the strands of the braid may be glued in place using a medical grade adhesive such as cyanoacrylate. In the embodiment shown in FIG. 1D, intermediate distal segment 146 is formed of a harder material that then surrounding segments, soft tip 148 and soft distal segment 144. The use of a harder material maintains the strands of the braids in position so that these strands do not migrate to the outer surface of sheath distal tip. In one embodiment, braid 154 is terminated approximately at the transition 160 between soft tip 148 and intermediate distal segment 146. For example, the distal end of braid, in one embodiment, ends in a region that is within approximately 0.07 cm from transition 160 in soft distal segment 144, or is within approximately 0.3 cm from transition in intermediate distal segment 146.

FIG. 1E is a perspective cutaway view of the sheath of FIGS. 1C and 1D. This view shows internal liner 152, braid 154, and a portion of sheath that, for exemplary purposes, is shown as shaft section 133. However, a similar view applies to intermediate and distal sections, 134 and 135, respectively. This figure illustrates the eight-by-eight continuous braid pattern discussed above. According to one embodiment of the invention, several strands of braid 162 are formed of metals that are more radio-dense than the others, and are therefore more visible under fluoroscopy. These strands provide a profile of sheath when viewed under a fluoroscope.

Sheath 130 of the current embodiment includes characteristics that make it ideal for placing leads and other IMDs within the coronary sinus or branch veins. For example, the segments at the distal end of sheath 130 are formed of a relatively soft material. This provides a very soft atraumatic tip that minimizes the chance of tissue damage. Additionally, the braid provides support to sheath shaft, making it more kink resistant as it is pushed through the vascular system during an implant procedure. Kink resistance is further enhanced by using transition section 134 to provide gradual changes between the stiffer shaft section 133 and soft distal section 135. As a result, sheath 130 can survive a ninety-degree bend without kinking when supported by a steerable EP catheter in the manner discussed in detail below. These same attributes provide for a sheath that is more pushable than prior art designs, make it easier to navigate the torturous curves of the venous system.

The foregoing attributes also provide a device that is easier to remove from the body after a lead or other IMD has been positioned at a final implant location. The soft distal section 135 and substantially straight profile of sheath 130 allow it to easily track over another device such as a lead to prevent the "whipping" effect that is commonly exhibited by prior art sheaths. This is particularly important when the sheath is withdrawn from the coronary sinus or branch vein, since a whipping motion can dislodge the lead, making it necessary to repeat the entire procedure.

Additionally, the sheath of the current invention is designed to be slittable. That is, the system uses braid materials that are slittable, yet provide maximum backup support and pushability to the sheath body. This allows sheath 130 to be slit away from leads and other IMDs having larger connectors, including IS-1 standard connectors. The selection of braid materials maintains this slitting capability without sacrificing the beneficial properties that make the sheath easier to navigate.

Finally, sheath 130 has an outer diameter that is small enough to be advanced within the coronary sinus and into branch veins. The very soft atraumatic tip allows this to be accomplished without damaging tissue. Additionally, the lubricious internal PTFE liner allows leads and other IMDs to be advanced within the sheath internal lumen when only a minimal amount of clearance is available.

The inventive sheath described above may be used in combination with the components, including a balloon catheter, a deflection mechanism, and/or a micro-deflection mechanism described below to facilitate placement of leads and other devices within the coronary sinus and branch veins. Various exemplary methods of using the sheath are further discussed below.

Balloon Catheter

Turning now to FIGS. 2A-2B, an exemplary balloon catheter 200 as may be used within the sheath of the present invention is shown in side view and distal cross-sectional view, respectively. This catheter is largely similar to the guiding catheters disclosed in U.S. Pat. Nos. 6,021,340 and 5,775,327 to Randolph et al, the entirety of each of which are incorporated herein by reference, as well as the VUEPORT family of balloon occlusion guiding catheters sold by Cardima, Inc. of Fremont Calif.

Catheter 200 is designed to pass through the central lumen 104 of the delivery sheath discussed above, and reach the therapeutic site as a combined unit with sheath and deflection mechanism 300.

As shown in FIGS. 2A and 2B, balloon catheter 200 generally includes an elongated shaft 202, a distal shaft section 204, a proximal shaft section 206, and an inner lumen 208. A female luer lock 210 may be disposed on the proximal end of shaft 202 and secured by a suitable adhesive 212, such as UV-curable Loctite 4201.

A distal port 214 is provided in the distal end 216 of the catheter shaft that is in fluid communication with the inner lumen 208. Proximal of distal end 216 is an occlusion balloon 211 axially disposed in the distal section 204 about catheter shaft 202. The catheter shaft 202 is provided with an inflation lumen 209 that extends through the shaft 202 to the interior of the balloon 211 to direct inflation fluid therein.

On the proximal end of catheter 200, proximal to luer lock 210, is a multiarm adapter or hub 222 that terminates in a Y-adapter or hemostasis valve 232 and a proximal port 218 for passage of a deflection mechanism therethrough as described later.

A first sidearm or port 224 on adapter 222 (shown in partial cross section in FIG. 2A) facilitates introduction of inflation fluid into inflation lumen 209. A stopcock 228 on first sidearm 224 that allows balloon 221 to stay inflated once the proper volume of fluid (such as air) has been introduced via syringe 230 is disposed adjacent stopcock 228. Inflation lumen 209 is disposed in port 224 and extends distally into shaft 224 to facilitate inflation of balloon 211 as described above.

A second sidearm or port 226 may also be disposed on hub 222, and may be in direct fluid communication with large inner lumen 208. Inner lumen 208 is used for housing devices such as a deflection mechanism or the like. Once balloon 211 is inflated, the second port 226 may be used for introducing contrast media or similar material through lumen 208 and out the distal port 214 for visualization of a section of interest in the body, such as an organ lumen or the cardiac venous system, for instance.

Not shown is a rotatable hemostatic valve (RHV) that may be housed in the proximal center port 218 and that can accept devices such as a deflection mechanism described below. This RHV is capable of sealing onto the deflection mechanism to prevent fluid leakage and may be part of a duostat modified to comprise a single RHV and two sideports. Other configurations, of course, are possible.

Shaft 202 of balloon catheter 200 is of a sufficient size so that it may readily pass through the lumen 104 of sheath 100. Ideally, we prefer the outer diameter of shaft 202 to be between approximately 0.050 inch and 0.100 inch. More preferably, it is between 0.060 inch and 0.080 inch, and most preferably is about 0.074 inch.

The diameter of inner lumen 208 preferably is large enough to allow free passage of contrast media or other material therethrough so that venograms and similar diagnostic procedures may be readily accomplished. It should also be large enough for the passage of a deflection mechanism as discussed below in greater detail. Finally, lumen 208 should allow the free passage of contrast media or other agents therethrough while occupied by a device such as a deflection mechanism. In general, we prefer that inner lumen have a diameter of between 0.030 inch and 0.080 inches, and is preferably about 0.048 inch. Likewise, inflation lumen 209 preferably has a diameter of between about 0.005 inch and 0.020 inch, and preferably is about 0.014 inch.

The balloon catheter shaft 202 preferably comprises PEBAX tubing having a durometer hardness of between about 60 D and 80 D, preferably about 72 D. Preferably, shaft proximal section 206 has a heat shrink tubing disposed on the outer surface thereof. Preferably, this heat shrink tubing is polymeric and is comprised of clear polyolefin or the like. Distal tip 216 is preferably a soft, atraumatic tip made of a relatively flexible polymeric material similar in composition and stiffness to distal tip 112 of sheath 100. In one embodiment, distal tip is radiopaque.

The working length of balloon catheter shaft 202, which includes the distal tip 216, distal section 204, and proximal section 206, should be between about 50 cm and 90 cm, although it may be longer or shorter depending upon the application. We especially prefer a working length of approximately 70 cm, which can accommodate a distal tip 216 of approximately 0.5 cm, a distal section 204 of approximately 6 cm, and a proximal section 206 of approximately 63.5 cm.

The length of the entire catheter 200 in this embodiment (the working length of shaft 202 and the components disposed proximal of proximal section 206 discussed above) should be about 77.5 cm. In general, we prefer that the balloon catheter shaft 202 be between about 15 cm and 20 cm longer than the above-described sheath of the current invention.

Of course, the absolute and relative lengths of each component of catheter 200 may vary considerably. The particular application in which catheter 200 and the entire system of the present invention is to be used will dictate the particular dimensions and materials for it's various components (as well as each of the components of the inventive system) described herein.

Occlusion balloon 211, when inflated, should have a diameter sufficient to seal the coronary sinus ostium. This inflated diameter will typically be between about 0.2 inch and 1.0 inches, and more preferably, between about 0.4 inch and 0.8 inches. We prefer balloon 211 to comprise an inelastic or elastic polymeric material. Polyurethane such as PELLETHANE 80 A (Shore) is especially preferable. The inner diameter of the uninflated balloon 211 typically will be between about 0.04 inch and 0.08 inches, and more preferably between about 0.056 inch and 0.070 inches. The balloon wall thickness typically will be between about 0.002 inch and 0.006 inches, and more preferably about 0.004 inches. Finally, the balloon 211 length typically will be between about 6 mm and 14 mm, and more preferably between about 8 mm and 12 mm.

Deflection Mechanisms and Micro-Deflection Mechanism

The deflection mechanism and the micro-deflection mechanism are two separate components that may be used in conjunction with the sheath of the present invention. Deflection mechanism 300 is designed for use in the balloon catheter 200, and is similar in many respects to the micro-deflection mechanism 400, only larger. Micro-deflection mechanism 400 is designed for use in a variety of applications where precise control and deflection of a device such as a lead, electrophysiology catheter, or other similar IMDs, is needed. Its small size relative to deflection mechanism 300 renders it useful in a wide range of applications in which its small size and flexibility may be relied upon.

FIG. 3 is a plan view illustrating components of both the deflection and micro-deflection mechanisms, although it will be described in terms of the deflection mechanism 300 for discussion purposes. Deflection mechanism 300 generally comprises a proximal section 304, a distal section 306, and a distal tip 308. Adjacent the proximal section 304 is handle 310, a preferred variation of which is shown in detail in FIGS. 4A and 4B.

Deflection mechanism 300 is designed to be placed through proximal port 218 of the balloon catheter 200 and into the inner lumen 208 such that the deflection mechanism distal tip 308 generally reaches distal section 204, and preferably distal tip 216, of balloon catheter shaft 202. When the handle 310 is activated, the distal section 306 of deflection mechanism 300 deflects in a predetermined fashion, thus deflecting the distal section 204 of the balloon catheter in a similar fashion. In this way, balloon catheter 200 (or any device into which deflection mechanism 300 is disposed) may be torqued to conform to the particular lumen or cavity into which it is disposed.

Shaft 302 of deflection mechanism 300 comprises a tubular member such as hypotube 312, preferably made of metallic biocompatible material such as medical grade stainless steel, titanium, nitinol, alloys of these, or any suitable material as known to those of skill in the art. Hypotube 312 preferably has an outside diameter small enough to fit within inner lumen 208 of catheter 200 and is preferably less than 0.048 inch. As shown in FIG. 3, hypotube 312 is beveled to form a strain relief 316 at the distal end of hypotube 312. Of course, this particular configuration of hypotube 312, as well as other aspects of the FIG. 3 deflection mechanism 300, is merely exemplary. Other configurations that serve the purposes of this invention are within the scope of this disclosure as well.

Disposed within a central lumen of hypotube 312 is a pull wire 320, which can be a stainless steel, titanium, nitinol or other metal or alloy or even polymeric wire which when pulled activates the deflection of distal section 306 of deflection mechanism 300. Pull wire 320 is attached to a flat spring 322, which is disposed in the distal section 306 of deflection mechanism 300. Spring 322 is attached to hypotube 312 using any suitable attachment method, such as welding, brazing, soldering, adhesives, or the like as is known to those of skill in the art. Spring 322 may be brazed to hypotube 312 along braze zone 314 as seen in FIG. 3. Likewise, any similar suitable attachment techniques may be used to attach pull wire 320 to spring 322. In one embodiment, the pull wire and spring are brazed to one another in braze zone 318 as seen in FIG. 3.

Distal deflection region 306 is preferably covered with compliant polymeric medical grade tubing, such as polyester, PEBAX, and tetrafluoroethylene. Especially preferred is a polymer of tetrafluoroethylene hexafluoropropylene and vinylidene fluoride known by its acronym as THV. This prevents fluid intrusion into the deflection mechanism.

In an especially useful variation of the invention in which the system is used for implanting a lead, the balloon deflection mechanism 300 will be of sufficient diameter to provide rigidity to the balloon catheter 200 during introduction into the coronary sinus ostium. The curve reach and deflection range should be sufficient to provide easy introduction into the coronary sinus ostium, and the entire assembly should provide adequate pull strength to deflect and torque the distal portion 204 of balloon catheter shaft 202 during manipulation into the coronary sinus ostium.

Figure 4B:
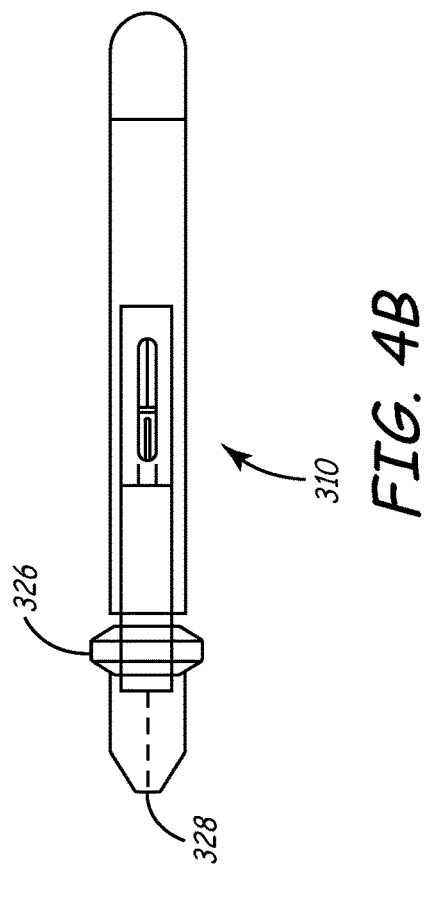
FIGS. 4A-4B are various views of a handle as may be used with the deflection and micro-deflection mechanisms of FIG. 3.
Figure 4A:
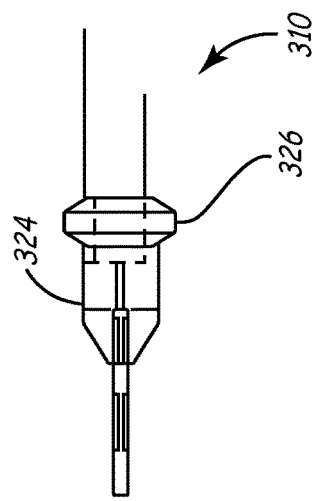

Turning now to FIGS. 4A-4B, a useful variation of handle 310 for manipulating deflection mechanism 300 is shown. Handle 310 includes body 324 and activation mechanism 326. Activation mechanism 326 may be manipulated by pushing distally or pulling proximally along a longitudinal axis of handle 310. The machined parts of these components may be polymeric. For example, a thermoplastic such as the acetyl homopolymer DELRIN (E.I. du Pont de Nemours and Company, Wilmington, Del.) may be used for this purpose. The molded parts may be formed of polymeric materials such as ABS (acrylonitrile butadiene styrene) or the like. A proximal end of pull wire 320 is disposed in a central lumen 328 of handle 310 and affixed into handle by means known to those of skill in the art.

Handle 310 is preferably lightweight and ergonomically configured for simple, one-handed operation. The deflection range (the maximum angular displacement the distal tip 308 undergoes when displaced from a straight and undeflected zero-degree position) may be between about 90 degrees and 180 degrees, preferably between about 100 degrees and 135 degrees. Further details of the features and versatility of distal section 306 will be described in greater detail below, as well a detailed description of how deflection is achieved.

Figure 5:
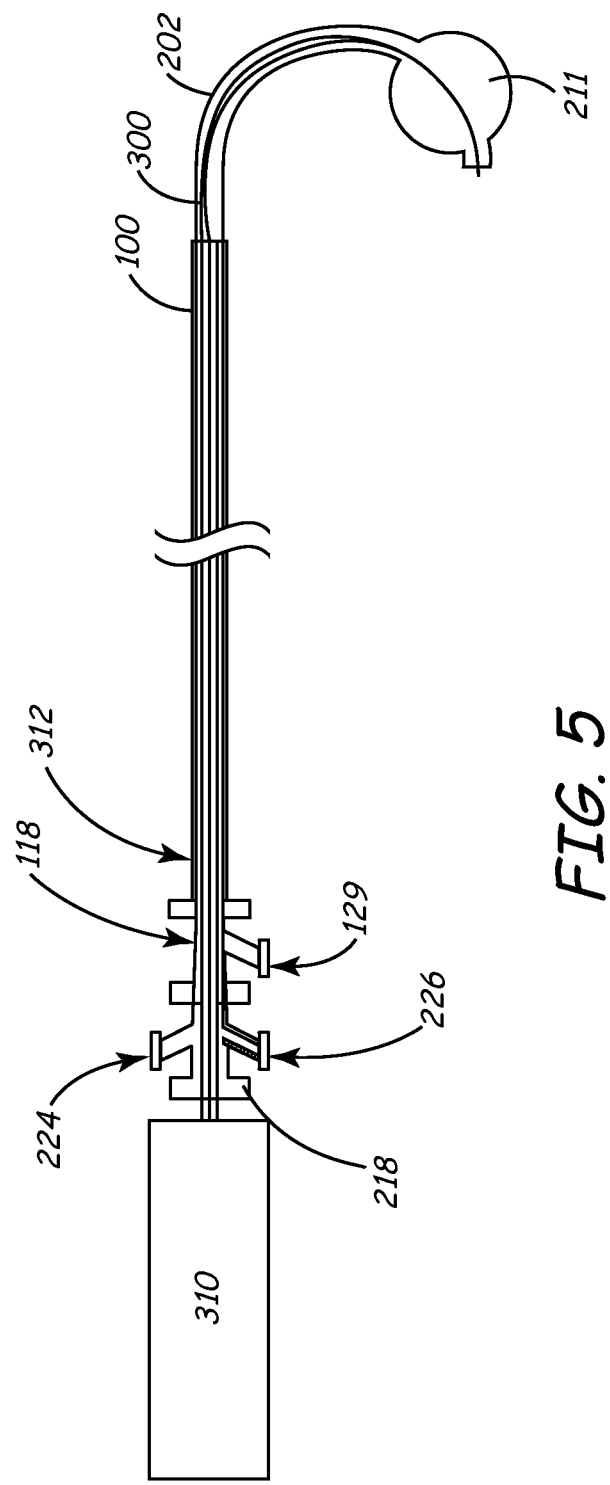
FIG. 5 is a cross-sectional side view of a deflection mechanism, an outer sheath, and a balloon catheter with an inflated distal balloon and a deflected distal end.

FIG. 5 depicts in partial cross-section three components that may be used with the inventive sheath. Deflection mechanism 300 with handle 310 is shown disposed in the inner lumen of balloon catheter shaft 202 via the proximal port 218 as previously described. In turn, the combination deflection mechanism 300 and balloon catheter 200 are disposed in the lumen 104 of sheath 100 (FIGS. 1A and 1B). I may be noted that any embodiment of the sheath, including that shown in FIGS. 1C and 1D, may be used in this manner. In FIG. 5, the distal section of balloon catheter shaft 202 is shown in a deflected state via the action of the hypotube/pull wire mechanism. Notice also that distal balloon 211 is inflated with fluid provided through balloon fluid port 224. An RHV 118 for outer peel-away sheath 100 as discussed herein is seen as a flush port 129 disposed on RHV 118. For purpose of clarity, sheath hub 114 is not shown.

In general, there is no limit to the size of the deflection mechanisms described herein. All of the related components are readily scalable to larger or smaller sizes than those disclosed here as would be apparent to one of ordinary skill in the art and as the particular application demands.

Turning now to a more specific discussion of micro-deflection mechanism 400 depicted generally in FIG. 3, the features of this element are largely similar to those of deflection mechanism 300. The features are generally smaller so that they may be used within devices such as leads, electrophysiology catheters, and the like as will be described below.

The micro-deflection mechanism utilizes a hypotube configuration as shown in FIGS. 7A, 7B, and 8A through 8E. We prefer the outer diameter of the micro-deflection mechanism hypotube (not shown) to be between about 0.012 inch and 0.030 inch; preferably between about 0.014 inch and 0.026 inch; most preferably about 0.015 inch. This will allow introduction of the hypotube into a conventional IS-1 lead connector, as well as allow for movement of the hypotube within the entire length of the central lumen of a lead body without causing any undue stress or damage to any of the lead or catheter components.

We also prefer that the micro-deflection mechanism 400 pull wire, which is also preferably stainless steel or nitinol, have an outer diameter of between 0.005 and 0.015 inches, and more preferably between about 0.006 and 0.010 inches. Most preferably, the outer diameter is about 0.008 inch.

During deflection, we prefer that the distal-most 10 mm to 30 mm of the assembly 400 deflect, which in a preferred application, will allow the lead into which assembly 400 is placed to engage the coronary sinus ostium. Due to the smaller size and greater maneuverability, assembly 400 may deflect through angles as high 360 degrees and even 450 degrees or more. Such a high angular deflection capability allows the mechanism 400 (and the device into which it may be deployed) to create a tight loop. These high-angle deflections are especially useful in electrophysiology applications in which the micro-deflection mechanism 400 may be deployed in a mapping/ablation microcatheter to effect circumferential ablation patterns and the like in areas such as the cardiac pulmonary vein.

FIGS. 6A-6D depict various components of an especially useful variation of micro-deflection mechanism 400 handle 414. As shown in FIG. 6A, handle 414 includes a body 416 and an activation mechanism 418 that may be manipulated by pushing distally or pulling proximally axially along a longitudinal axis of handle 310. The handle has a relatively small length that may be in the range of about 2 inches. This scales well with the other, smaller components of micro-deflection mechanism 400, and also allows for simple, one-hand fingertip operation by a physician. Of course, the sizes may be sized as needed in a manner discussed above.

Micro-deflection mechanism 400 can be used to replace the fixed-curve stylet generally used to provide a deflectable lead or catheter. This deflectable lead or catheter may be more precisely placed in the targeted region of the cardiac venous system, overcoming the problems of state-of-the-art systems. In addition, the micro-deflection mechanism may be used in conjunction with the inventive sheath described above and other components discussed herein for deflectable electrophysiological catheters.

Turning now to features that are common to both the deflection mechanism 300 and micro-deflection mechanism 400 (hereinafter referred to in this generic discussion as simply "deflection mechanism"), each operates on the same principal based on a hypotube/pull wire assembly. The pull wire runs through the middle of the hypotube and is attached, via brazing or the like, at the distal end of the deflection mechanism.

The hypotube is allowed to deflect in a predetermined pattern by a series of slots, or perfs, cut into the hypotube distal section. U.S. Pat. No. 5,507,725 to Savage et al, U.S. Pat. Nos. 5,921,924 and 5,441,483 both to Avitall, U.S. Pat. No. 5,868,768 to Wickerski, U.S. Pat. No. 5,304,131 to Paskar, the entirety of each which are hereby incorporated by reference, describe various medical devices in which some type of notch is used to effect deflection FIGS. 7 and 8 depict two variations of notch patterns that are useful in the present invention. Because of the scalability of these features, they are useful in both the deflection assembly 300 as well as micro-deflection assembly 400.

In reference to FIGS. 7 and 8, and the following discussion, note that due to the drawing space constraints, the "proximal section" of the hypotube refers to a portion of the deflection mechanism that is proximal only in that it is disposed proximal to the corresponding distal section. It is possible that a considerable length of the hypotubes depicted in FIGS. 7 and 8 exists proximal to the so-marked "proximal section".

In FIGS. 7A and 7B, two hypotube/pull wire combinations are shown in top and side views, starting from the top of the page, respectively. FIG. 7A depicts an assembly 700 in which a pull wire 704 is brazed, soldered, or otherwise affixed to the distal end of hypotube 702 at hypotube distal section 708. Note that pull wire 704 is deployed inside hypotube 702. The pull wire is disposed in the interior of hypotube 702 all the way to the hypotube distal section 708 where it is affixed to hypotube 702 as described above. In general, pull wire 704 is affixed in handle 310 such that when the handle is activated, hypotube distal section 708 will deflect on the same side on which notches 710 (or as discussed below, the reduced wall thickness of hypotube) are located.

Each notch or perf 710 is progressively deeper as one moves from the proximal end 706 of hypotube 702 to the distal end 708. This particular feature will cause the hypotube to deflect in a smooth consistent curve. Note that the spacing between notches 710 is constant, and the only dimension of each notch 710 that changes its depth. The width remains constant. Each of these parameters may vary as performance requires.

Further, the centroids of each notch are aligned along a single, straight liner longitudinal axis as one moves from proximal section 706 to distal section 708. This axis along which the notches are aligned may be nonlinear. For instance, the axis may be sinusoidal to provide a serpentine deflection profile, with a constant or varying pitch, or the axis may have some other curvilinear or even stepwise shape. Regardless of whether the notch centroids are aligned along a linear or nonlinear axis, the centroid of each notch does not have to line up along such an axis.

Note also that the distance between adjacent notches as one moves from one end of a notch to the other end of hypotube of FIG. 7A remains constant. That is, the longitudinal axes of the notches are parallel to one another. This aspect of the notches or perfs may also change depending upon the application.

Another variable that may affect the shape and performance characteristics of the assembly 700 is the depth to which the notches 710 are cut into the hypotube. For instance, in the assemblies of FIGS. 7A and 7B, the notches are cut completely through the wall thickness of hypotube 702. This need not be the case. It is within the scope of the invention to provide notches in hypotube 702 in which a discrete amount of material is removed from the hypotube without penetrating through the hypotube thickness. A wide variety of depth profiles and patterns in etching each notch are therefore envisioned.

Taking this concept one step further, hypotube 702 need not contain a series of notches or perfs to achieve the desired preferential distance deflection shape and response. For instance, it is within the scope of the invention to preferentially machine or etch the bulk of hypotube 702 in an asymmetric fashion so that when the pull wire 704 is activated, the distal section 708 of hypotube 702 deflects in a predetermined pattern. In other words, the wall thickness of hypotube 702 can be made to vary a function of length and/or circumferential position in patterns ranging from a simple tapering pattern to complex patterns in which correspondingly intricate and complex deflection shapes and resources may be had. Such a concept can be used alone or in conjunction with the use of notches or perfs as described herein.

Each of the parameters described above, as well as other parameters such as hypotube wall thickness, material selection, etc. may be chosen to effect a particular deflection pattern and response depending upon the application for which the hypotube/pull wire assembly (such as assembly 700) is intended. Furthermore, variations in many of these parameters from notch-to-notch may also be made. For instance, one notch may have a rectangular profile, while another notch on the same hypotube may have a circular profile, etc.

Software may be utilized to aid the designer, by way of mathematical algorithms and the like, to ascertain the optimal profile for hypotube 702 given a desired deflection shape, etc. For instance, a designer may be able to choose the application for which the assembly is to be used, and the software may select a number of alternative shapes from which the designer may choose. Once a deflection shape is chosen, the software will then calculate the optimal hypotube profile.

FIG. 7B shows an assembly 750 in which hypotube 752 and pull wire 754 are arranged in a similar fashion to those described above and shown in FIG. 7A. The only difference in the assembly of FIG. 7B is that the constant spacing between the notches 756 is larger than that in the assembly of FIG. 7A. This increased but constant spacing between notches 756 results in hypotube 752 being slightly heavier, since less material has been cut away from the hypotube. When assembly 750 is deflected, this means that distal section 760 will deflect through a smaller angle with a larger curve diameter (although the deflection shape will generally be similar as that of the deflected assembly 700 due to the similar size, shape, and orientation of the notches in each assembly) than that experienced by assembly 700 in FIG. 7A for a given deflection force.

Figures 8A, 8B:
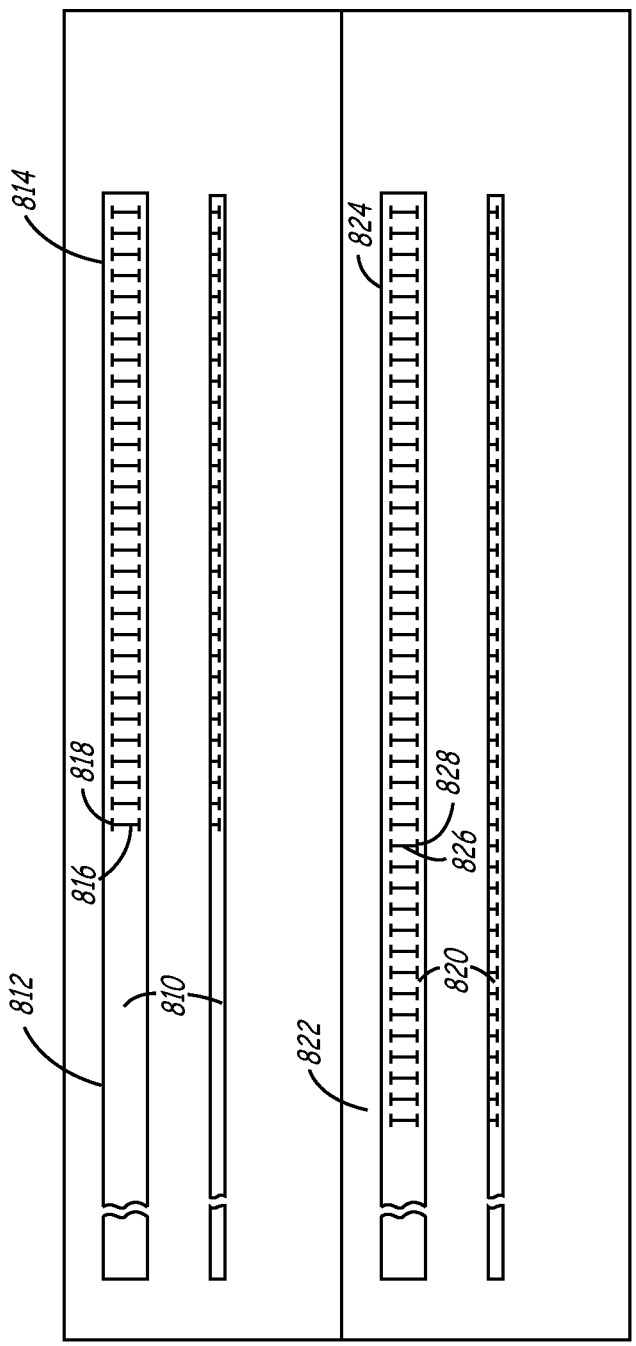
FIGS. 8A-8D are additional embodiments of deflection and micro-deflection mechanisms, detailing additional notch configurations.

Turning now to FIGS. 8A through 8E, additional variations of a notch pattern are shown (the pull wire is omitted for clarity). In FIG. 8A, hypotube 810 with proximal section 812 and distal section 814 contains a series of linear notches 816 similar to those of FIGS. 7A and 7B, except that each end of notches 816 contain a secondary notch 818 oriented generally perpendicular to notch 816. This notch design causes the distal section 814 of hypotube 810 to deflect in a similar fashion as described above, possibly with a tighter curve diameter.

The hypotube of FIG. 8B is identical to that of FIG. 8A, except that the notch pattern begins closer to the proximal section 822 of hypotube 820. A longer length of hypotube distal section 824 will therefore deflect when activated by the pull wire.

Figure 8C:
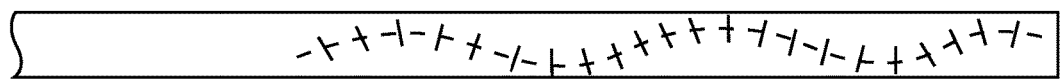

FIG. 8C is a plan view depicting an embodiment of deflection mechanism wherein the notches are arranged in a non-linear manner. For example, a sinusoidal pattern is depicted, although many other types of patterns are possible.

Figure 8D:
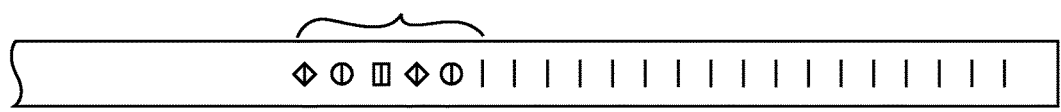

FIG. 8D is a plan view depicting an embodiment of deflection mechanism wherein the notches are of different shapes and sizes. For example, the notches may be circular, triangular, rectangular, or any other pattern desired to allow the deflection mechanism to assume a desired shape when tension is applied to the pull wire. The notches may all have a uniform shape and size, or alternatively, may have different shapes and/or sizes.

Figure 8E:
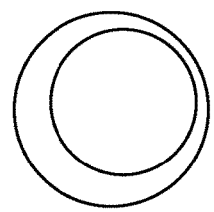
FIG. 8E is a cross-sectional view of a deflection and micro-deflection mechanism having a tubular member with an irregular wall thickness to provide a preferred bending direction.

FIG. 8E is a cross-sectional view depicting an embodiment of the deflection member wherein the hypotube has walls that are not of a consistent thickness. The thinner region of the wall defines a preferred bending direction when tension is applied to the pull wire. In one embodiment, both a thinner wall thickness and the creation of notches in the thinner region may be used to provide the deflection mechanism in the hypotube or other tubular member.

The notches or perfs described herein and shown in the figures, as well as the varying wall thickness of the hypotube, may be created by any means know to those of skill in the art. They may be machines by traditional, laser, electron-discharge, or similar machining methods, they may be chemically etched, etched using known photolithographic techniques, etc.

A particularly useful feature in the deflection mechanisms described herein is the active control feature of the deflection mechanism handle (both handle 310 as well as handle 414). Once the handle activation mechanism is engaged to deflect the distal section as described above, the deflection can be reversed only by the positive input of a user to disengage the same activation mechanism. In one embodiment of the deflection mechanism described above and shown in FIGS. 4A-4B and FIGS. 6A-6D, release of the activation mechanisms 326 and 418 after these mechanism are deployed results in the distal section remaining in a deflected position. Reversal of this deflection requires that the physician-user retract the activation mechanism, whereupon the distal section 306 will resume the undeflected state until the handle is activated once again. This feature allows the physician-user to manipulate other portions of the inventive system or to perform other tasks while the distal section 204 of balloon catheter 200, for example, remains in the intended deflected or undeflected state. Of course, it is within the scope of the invention to design the handle so that activation to deflect distal section is automatically reversed to return the distal portion to a default undeflected state. This may be accomplished by a bias spring or equivalent mechanism that activates when the physician releases the positive input causing the initial deflection. Such a design may also bias the distal end of the deflection mechanism to automatically reverse to a default deflected position.

Another feature common to both handles 310 and 414 is the presence of one or more limit stops that may be built into the handle. These limit stops are designed to prevent over-deflection of the deflection mechanism.

Deployment of Cardiac Lead

Figure 9:
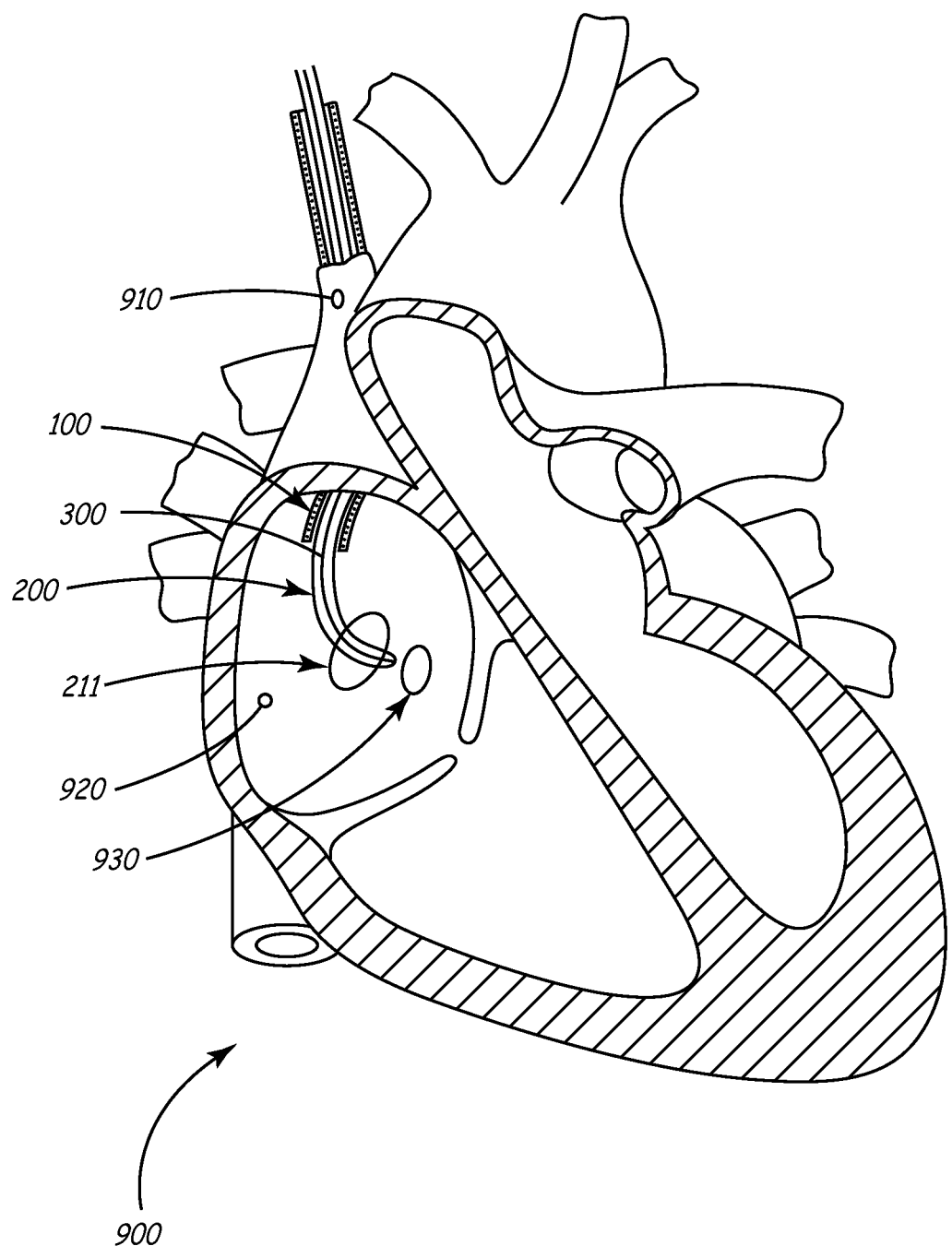
FIGS. 9-11 depict a method for accurately placing an endocardial lead into the cardiac venous system through the coronary sinus ostium using a system of the present invention.
Figure 10:
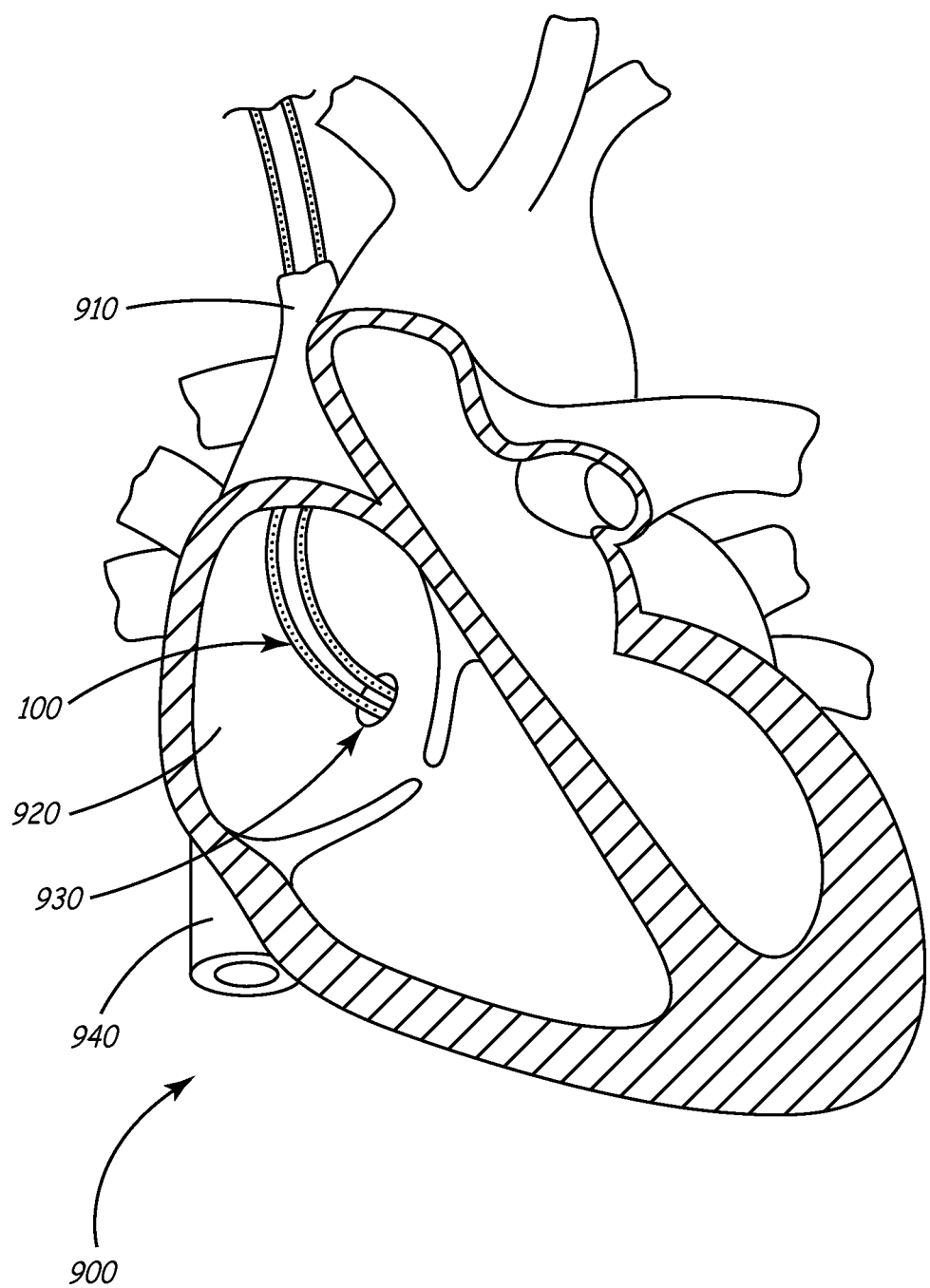
Figure 11:
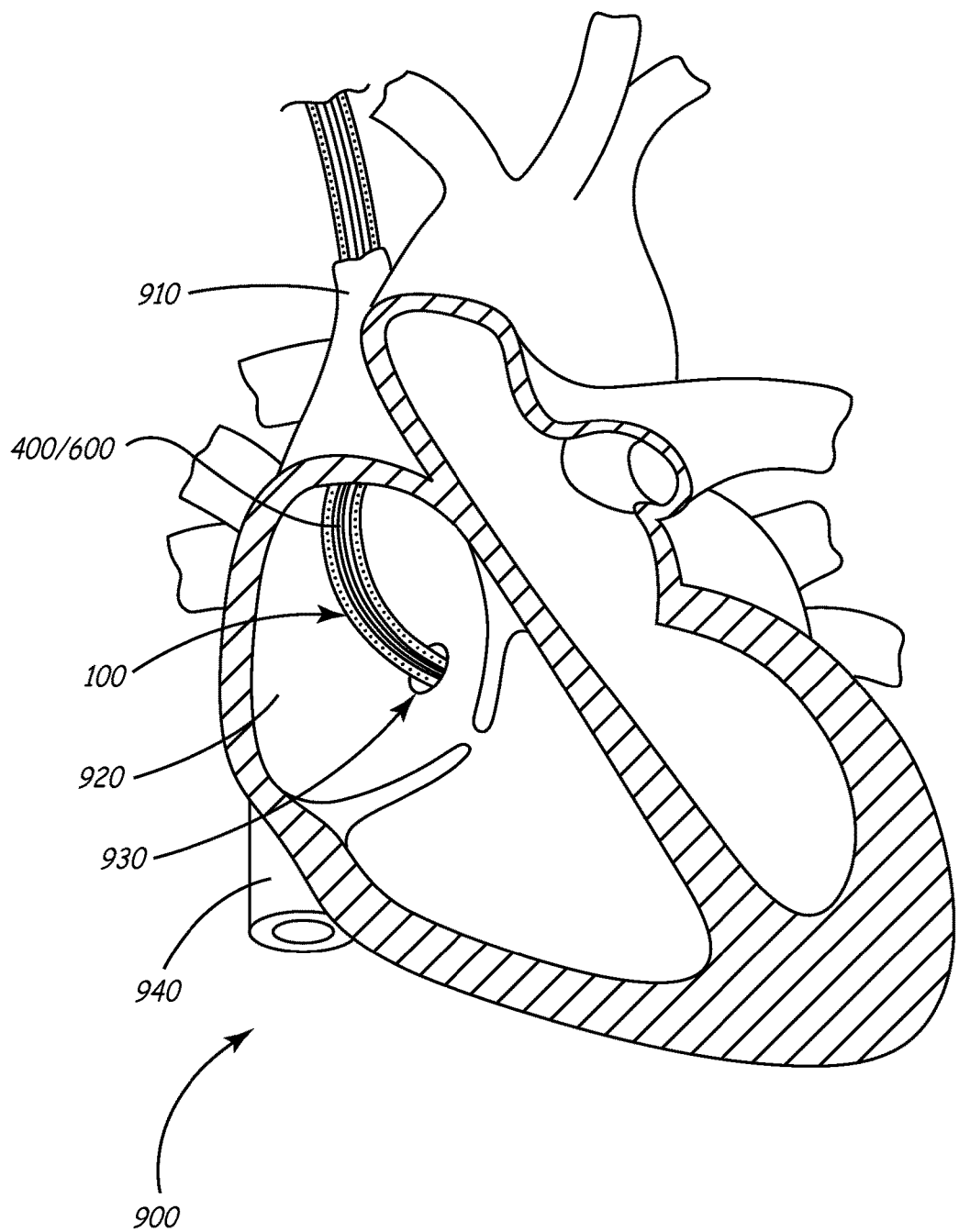

Turning now to FIGS. 9-11, a particularly useful application for the system herein described is shown and is discussed below. In particular, a method for intravascularly deploying the system into the coronary sinus, obtaining an occlusive venogram, and accurately subselecting a venous branch and placing a cardiac lead therein is described.

To prepare for the procedure, balloon catheter 200 is inserted within the lumen 104 of outer sheath to create a sheath/catheter combination. A deflection mechanism 300 is advanced into the large lumen 208 of the balloon catheter via proximal port 218 so that the distal tip 308 of the deflection mechanism shaft 308 is generally disposed in balloon catheter shaft 202 near shaft distal tip 216 as previously describe. This creates a combination sheath/catheter/deflection mechanism system as shown in FIG. 5. Typically, a portion of shaft 202 will extend out through and beyond the lumen 104 at the sheath 100 distal end 112 for some length.

This three-component system is introduced into the patient's venous system through the cephalic, subclavian or femoral vein via a conventional introducer as known to those of skill in the art. The physician uses the introducer to dilate the selected vein and then advances the system through the introducer into the selected vein.

Typically under fluoroscopic guidance, the physician navigates the three-component system through the vasculature to and through the superior vena cava 910 or inferior vena cava 940 (see FIG. 9) and into right atrium 920 of the heart. At this point, distal tip 216 of shaft 202 and distal balloon 211 engage the coronary sinus ostium. The deflection mechanism is used to help steer the shaft 202 distal tip 216 into place. Balloon 211 is then inflated, and contrast is injected into the coronary veins through the distal port 214 of shaft 202. This creates an occlusive venogram for visualizing the coronary veins in advance of placing the lead in the desired location.

Next, while balloon 211 is still in the coronary sinus, the sheath 100 is advanced into the coronary sinus over the catheter shaft 202 so that it may be available as a conduit for lead placement. Once the sheath 100 is in place, the balloon 211 is deflated and the balloon catheter 200 and the associated deflection mechanism 300 are proximally withdrawn from sheath 100, leaving sheath 100 alone in place in the coronary sinus as shown in FIG. 10.

Next, the micro-deflection mechanism 400 is placed into a central lumen of a lead 600 so that the deflectable distal section of micro-deflection mechanism 400 generally engages the distal section of the lead 600. The combination of these components is then advanced into the lumen 104 of sheath 100 and into the coronary sinus ostium as seen in FIG. 11. From here, the physician will activate the deflection mechanism to steer the lead/micro-deflection mechanism combination. In one embodiment, the micro-deflection mechanism may be used to subselect a venous branch into which the lead is to be permanently placed. Of course, the particular deflection shape and characteristics of micro-deflection mechanism have been selected by the physician for optimal use in navigating the venous system and creating the shape for the lead to assume during lead placement.

Once the lead 600 is placed and the pacing thresholds are acceptable, the RHV 118 is removed from the sheath and slid over the lead connector (alternatively, RHV 118 may be split). Next, preferably with the aid of a special slitting tool such as a customized razor blade attached to the sheath 100, the sheath 100 and hub 114 are split along score 126 as the sheath is pulled away from the lead 600 and removed from the body.

Micro-deflection mechanism 400 may be withdrawn from the lead 600, after which the lead 600 is the only component left in the body. Lead 600 remains in place, and may be coupled to a pulse generator, cardioverter/defibrillator, drug delivery device, or another type of IMD.

As discussed throughout the specification, the method outlined above is merely exemplary of one way to deploy a cardiac lead according to the present invention. For example, any embodiment of the inventive sheath may be employed in the above-described method, including sheath 130 (FIGS. 1C and 1D). Many alternative applications for the invention are likewise possible. Significant variations from this technique may occur within the scope of the present invention.

For example, in one embodiment, the deflection mechanism that is adapted to be inserted within the balloon catheter is a steerable catheter such as an electrophysiology (EP) catheter. One example of a catheter having a suitable steering mechanism is the Marinr catheter commercially available from Medtronic Corporation.

FIG. 12 is a plan view of a steerable catheter that may be used to navigate the balloon catheter 200 into the coronary sinus. The catheter 1000 is an anatomically-conforming, dual curve EP catheter used to sense electrical signals in the heart and associated vasculature. The catheter includes a shaft 1004 having an atraumatic distal end 1006 and a proximal end 1008. Shaft 1004 may have an outside diameter of less than approximately 0.093 inches and a length of about 50 mm to 110 mm. Proximal end 1008 is mounted to a handle 1010 having axially slidable manipulator rings 1012 and 1013, and a rotatable lateral deflection ring 1014 operably connected to proximal and distal manipulator wires carried by the body of the catheter. Sliding manipulator rings 1012 and 1013 cause a deflectable tip 1020 of catheter shaft 1004 to deflect as shown in FIGS. 12A and 12B between, for example, the solid-line and dashed-line positions of FIG. 12B. Rotating ring 1014 causes lateral deflection of tip 1020 through the torquing action of a core wire as shown in FIG. 12C.

A steerable EP catheter of the type shown in FIGS. 13A through 13C may be inserted within the inner lumen of the balloon catheter, which in turn, is inserted within the lumen 104 of the outer sheath 100 to create an alternative sheath/catheter combination. As previously described, this assembly may be advanced into the chambers of the heart. Next, the EP catheter distal tip may be advanced beyond the distal end of the outer sheath to guide the balloon catheter into the coronary sinus. The range of motion provided by the steerable catheter as noted above makes it particularly suitable for cannulating the coronary sinus so that the balloon catheter may then be used to obtain a venogram. Then the balloon catheter and the steerable catheter are removed from the sheath so that the sheath may be used to place an IMD with a microdeflection mechanism in the manner discussed above.

In yet another manner of using a sheath according to the current invention, steerable EP catheter 1000 may be preloaded into sheath 130 (FIGS. 1C and 1D). This sheath/catheter combination may then be advanced into the chambers of the heart, and the distal tip of this combination used to cannulate the coronary sinus. Alternatively, the EP catheter distal tip may be advanced beyond the distal end of sheath 130 to cannulate the coronary sinus, and the sheath distal end may thereafter be tracked over the EP catheter into the coronary sinus.

After the distal end of sheath 130 is seated within the coronary sinus, EP catheter 1000 may be withdrawn from inner lumen 152. In its place, a balloon catheter such as balloon catheter 200 may be advanced within the lumen to obtain a venogram in the manner discussed above. Thereafter, the balloon catheter is withdrawn from the body so that a lead may be advanced within the sheath lumen into the coronary sinus.

In one embodiment, the central lumen of lead 600 is pre-loaded with micro-deflection mechanism 400, or any type of navigational device such as a stylet or guidewire. The lead is then advanced through the lumen of sheath 130 into the coronary sinus ostium as generally shown in FIG. 11. The lead may then be directed into a branch vein of the coronary sinus using the pre-loaded device to provide guiding capabilities.

A method similar to that described in the foregoing paragraphs may be used with an over-the-wire lead similar to the 2187™ model lead commercially-available from Medtronic Corporation. In this instance, a guidewire may be advanced into the inner lumen of sheath 130 and beyond the sheath distal end. If desired, the guidewire may be used to sub-select a branch vein. An inner lumen of the lead may then be tracked over the guidewire into the coronary sinus or branch vein. In a similar embodiment, the guidewire may be preloaded into the lead inner lumen so that the combination may be advanced within the sheath lumen. The guidewire may then be advanced beyond the distal end of the sheath to sub-select a branch vein, and the lead may be tracked over the guidewire to the target destination.

In still another embodiment of the above method, sheath 130 is used to sub-select a branch vein of the coronary sinus instead of a guidewire or other micro-deflection mechanism. As discussed above, sheath 130 is provided with an extremely soft, flexible, atraumatic distal tip that minimizes risk of tissue perforation. Moreover, the sheath is sized for entry into the coronary sinus or a branch vein. Additionally, because of the inclusion of a braid such as braid 154 (FIG. 1D), sheath is very pushable. This combination of characteristics makes sheath 130 ideal for sub-selecting a branch vein prior to lead placement.

After a lead or other IMD is positioned at a target destination, sheath 130 may be withdrawn from the body. This may be accomplished by slitting the sheath using any commercially available slitting tool, as is necessary if the lead or other IMD being positioned by the sheath has a connector that is not small-profile. As discussed above, the construction of sheath 130 is specifically designed to be slittable despite the inclusion of braid 154.

Withdrawal of sheath 130 from the body is made easier by the use of soft materials within transition section 134 and distal section 135, and by the use of a substantially straight sheath configuration. As noted above, these features allow the sheath to track a lead body without exhibiting a "whipping" effect as may occur when the sheath exits the coronary sinus. This type of whipping motion is a common problem associated with prior art devices, and is known to cause lead dislodgement such that, in some instances, the entire procedure must be repeated.

According to another aspect of the invention, the system described herein may be used for deploying a wide array of devices other than leads in the coronary venous structure, the pulmonary venous structure, or any organ with large enough vessels for the introduction of the system. In addition, the system can be used in extravascular applications such as in the deployment of cochlear implants, in body cavities, muscle tissue, and the like.

The balloon catheter 200 can be used for the introduction of drugs or other media or agents within a very discrete region of a vessel. Note that the balloon on the balloon catheter 200 described herein is optional. The deflectable catheter may be used without a balloon, for improved access and maneuverability.

With respect to the micro-deflection mechanism 400, due to its ability to be scaled to a very small size, it may be used for interventions into the spinal column, tiny vessels in the brain, liver, kidney, or any other suitable organ. In addition, sensor such as electrodes for recording signals and possibly ablating tissue may be incorporated into the micro-deflection mechanism 400. Fiber optics for the introduction of light for visualization or optical recording or sensing may be incorporated into either deflection mechanism.

The deflection mechanism may also be used to deliver drugs or other therapeutic or diagnostic agents or materials as described above.

Many alterations and modifications may be made by those having ordinary skill in the art without departing from the spirit and scope of the invention. The illustrated variations have been used only for the purposes of clarity and should not be taken as limiting the invention as defined by the following claims.

What is claimed is:

1. A system for positioning implantable medical devices within the coronary sinus or a branch vein thereof, comprising:
   a substantially straight slittable sheath having an inner lumen, a shaft section, and a distal section that is distal to, and softer than, the shaft section, the sheath further including a slittable braid adjacent to at least a portion of at least one of the shaft section and the distal section, wherein the braid is formed of stainless steel, wherein the braid has an ultimate tensile strength of between approximately 200 and 250 kilo-pounds per square inch (ksi), wherein the braid has a pic count of between 35 and 55 pics per inch, and further wherein the braid is formed of a wire having a diameter of approximately 0.002 inches; and a steerable catheter having a shaft adapted to be inserted within the inner lumen of the sheath.

2. The system of claim 1, wherein the steerable catheter is an electrophysiology catheter.

3. The system of claim 1, and further comprising an internal liner adjacent at least a portion of the inner lumen.

4. The system of claim 3, wherein the internal liner is formed of a lubricious material.

5. The system of claim 4, wherein the lubricious material is selected from the group consisting of PolyTetraFluoro-Ethylene (PTFE), PolyVinylDieneFluoride (PVDF), and High-Density PolyEthylene (HDPE).

6. A sheath apparatus for receiving a steerable catheter to position implantable medical devices within the coronary sinus or a branch vein thereof, wherein the sheath apparatus comprises a substantially straight slittable sheath extending from a proximal end to a distal end defining an inner lumen, wherein the slittable sheath comprises:

a shaft section;

a distal section distal to the shaft section at the distal end of the sheath, wherein the distal section comprises a soft tip extending from a transition location along the distal section to the distal end of the sheath;

a slittable braid extending along the shaft section and at least a portion of the distal section, the slittable braid terminating at a distal end thereof approximately at the transition location, wherein the braid is formed of stainless steel, wherein the braid has an ultimate tensile strength of between approximately 200 and 250 kilo-pounds per square inch (ksi), and further wherein the braid has a pic count of between 35 and 55 pics per inch;

an internal liner adjacent at least a portion of the inner lumen and extending along the shaft section and terminating within the distal section of the sheath beyond the distal end of the slittable braid.

7. The sheath apparatus of claim 6, wherein the internal liner is formed of a lubricious material.

8. The sheath apparatus of claim 7, wherein the lubricious material is selected from the group consisting of PolyTetraFluoroEthylene (PTFE), PolyVinylDieneFluoride (PVDF), and High-Density PolyEthylene (HDPE).

9. The sheath apparatus of claim 6, wherein the inner lumen has an inner diameter ranging from about 0.86 to 0.106 inches.

10. The sheath apparatus of claim 6, wherein the slittable braid comprises one or more strands formed of a material more radio-dense than the other strands of the slittable braid.

11. The sheath apparatus of claim 10, wherein the one or more strands of a material more radio-dense are more visible under fluoroscopy than the other strands of the slittable braid.

12. The sheath apparatus of claim 10, wherein the one or more strands of a material more radio-dense provide a profile of the sheath when viewed under a fluoroscope.

* * * * *